US009371348B2

(12) United States Patent
Dmochowski et al.

(10) Patent No.: US 9,371,348 B2
(45) Date of Patent: Jun. 21, 2016

(54) PHOTOCLEAVABLE OLIGONUCLEOTIDE AND USES THEREOF

(75) Inventors: Ivan Dmochowski, Philadelphia, PA (US); XinJing Tang, Philadelphia, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 1491 days.

(21) Appl. No.: 11/987,128

(22) Filed: Nov. 27, 2007

(65) Prior Publication Data

US 2008/0227742 A1 Sep. 18, 2008

Related U.S. Application Data

(60) Provisional application No. 60/861,087, filed on Nov. 27, 2006, provisional application No. 60/881,165, filed on Jan. 19, 2007.

(51) Int. Cl.

| | | |
|---|---|---|
| C12Q 1/68 | (2006.01) | |
| C12P 19/34 | (2006.01) | |
| C07H 1/00 | (2006.01) | |
| C07H 21/00 | (2006.01) | |
| C12N 15/11 | (2006.01) | |

(52) U.S. Cl.
CPC .................. C07H 1/00 (2013.01); C07H 21/00 (2013.01); C12N 15/111 (2013.01); C12N 2310/11 (2013.01); C12N 2310/53 (2013.01); C12N 2320/50 (2013.01)

(58) Field of Classification Search
USPC ......... 435/6, 91.1, 91.31, 455, 6.11, 6.1, 968; 514/44; 536/23.1, 24.5, 25.32, 26.6, 536/25.3; 548/544
See application file for complete search history.

(56) References Cited

U.S. PATENT DOCUMENTS

| | | | |
|---|---|---|---|
| 2004/0146516 A1* | 7/2004 | Roben et al. ............... | 424/178.1 |
| 2005/0059028 A1* | 3/2005 | Nguyen et al. .................... | 435/6 |
| 2005/0282203 A1 | 12/2005 | Nguyen et al. | |
| 2006/0008907 A1* | 1/2006 | Friedman et al. ............ | 435/455 |
| 2007/0248960 A1* | 10/2007 | Rees ................................... | 435/6 |
| 2012/0328668 A1* | 12/2012 | MacLachlan et al. ........ | 424/400 |

OTHER PUBLICATIONS

Crooke, S., Ann Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature Rev. , vol. 1, pp. 503-514 (2002).*
Jang et al., Expert Rev. Medical Devices, vol. 1, No. 1, pp. 127-138 (2004).*
Paroo et al., Trends in Biotech., vol. 22, No. 8, pp. 390-394 (2004).*
Ghosn et al., Photochemistry and Photobiology, vol. 81, pp. 953-959 (2005).*
C. Cazenave, C. Stein, N. Loreau, N. Thuong, L. Neckers, C. Subasinghe, C. Helene, J. Cohen, J. Toulme, Nucleic Acids Res. 1989, 17, 4255.
M. Kozak, Proc. Natl. Acad. Sci. USA 1986, 84, 2850.
J. B. Opalinska, B. Machalinski, J. Ratajczak, M. Z. Ratajczak, A. M. Gewirtz, Clin. Cancer Res. 2005, 11, 4948.
J. Li, B. Bourdelat-Parks, J. H. Boatright, R. M. Wartell, Biochemistry 2003, 42, 10945.
S. G. Chaulk, A. M. MacMillan, Nucleic Acids Res. 1998, 26, 3173.
T. L. H. Jason, J. Koropatnick, R. W. Berg, Toxicol. Appl. Pharmacol. 2004, 201, 66.
M. Rubenstein, P. Tsui, P. Guinan, Drugs Fut. 2004, 29, 893.
W. Stec, G. Zon, W. Egan, B. Stec, J. Am. Chem. Soc. 1984, 106, 6077.
J. C. Hanvey, N. J. Peffer, J. E. Bisi, S. A. Thomson, R. Cadilla, J. A. Josey, D. J. Ricca, C. F. Hassman, M. A. Bonham, K. G. Au, S. G. Carter, D. A. Bruckenstein, A. L. Boyd, S. A. Noble, L. E. Babiss, Science 1992, 258, 1481.
J. Summerton, Biochim. Biophys. Acta—Gene Struct. Express. 1999, 1489, 141.
L. Wang, C. J. Yang, C. D. Medley, S. A. Benner, W. Tan, J. Am. Chem. Soc. 2005, 127, 15664.
D. Matsunaga, H. Asanuma, M. Komiyama, J. Am. Chem. Soc. 2004, 126, 11452.
B. Ghosn, F. R. Haselton, K. R. Gee, W. T. Monroe, Photochem. Photobiol. 2005, 81, 953.
L. Kröck, A. Heckel, Angew. Chem., Int. Ed. Engl. 2005, 44, 471.
S. Shah, S. Rangarajan, S. H. Friedman, Angew. Chem., Int. Ed. Engl. 2005, 44, 1328.
H. Ando, T. Furuta, R. Y. Tsien, H. Okamoto, Nat. Genet. 2001, 28, 317.
A. Yamazawa, X. Liang, H. Asanuma, M. Komiyama, Angew. Chem., Int. Ed. Engl. 2000, 39, 2356.
X. Bai, Z. Li, S. Jockusch, N. J. Turro, J. Ju, Proc. Natl. Acad. Sci. U.S.A. 2003, 100, 409.
X. Tang, J. L. Richards, A. E. Peritz, I. J. Dmochowski, Bioorg. Med. Chem. Lett. 2005, 15, 5303.
X. Tang, I. J. Dmochowski, Org. Lett. 2005, 7, 279.
Egholm M et al. "PNA hybridizes to complementary oligonucleotides obeying the Watson-Crick hydrogen-bonding rules." Nature. Oct. 7, 1993;365(6446):566-8.
Nielsen P et al. "Synthesis of 2'-0,3'-C-linked bicyclic nucleosides and bicyclic oligonucleotides." J. Chem. Soc. Perkin Trans. 1997 1, 3423.
Koshkin A et al. "Novel Convenient Synthesis of LNA [2.2.1] Bicyclo Nucleosides." Tetrahedron Letters 1998. 39, 4381.
Singh SK et al. "LNA (locked nucleic acid): synthesis and high-affinity acid recognition." 1998 Chem Commun (4).

* cited by examiner

Primary Examiner — Jane Zara
(74) Attorney, Agent, or Firm — Mark S. Cohen; Pearl Cohen Zedek Latzer Baratz LLP

(57) ABSTRACT

This invention relates to methods and compositions of oligonucleotide constructs having a photocleavable linker. Specifically, provided herein are methods and compositions utilizing a photocleavable linker, which when exposed to light modulates the expression of genes.

12 Claims, 21 Drawing Sheets

A

B
Conjugate

CCAACGTTTCGGACCGTATT(CH$_2$)$_3$-S-PC-NH-(CH$_2$)$_6$-AATACGGTCCGAGGTACCAA antisense ODN (asODN)                          sense (blocking) ODN
          (Seq. Id. No. 1)                                       (Seq. Id. No. 14)

RNA target                              PC linker

RNA-15: AAUACGGUCCGAAAC
          (Seq. Id. No. 15)
RNA-20: AAUACGGUCCGAAACGUUGG
          (Seq. Id. No. 16)
RNA-40: CUUGUACAGA<u>AAUACGGUCCGAAACGUUGG</u>UCUGUUAUUG
          (Seq. Id. No. 17)

A

B

C

Negatively charged PNA (ncPNA)

(Seq. Id. No. 27) (Cy5)-GTTTCGGACCGTATT-S⌒PL (Seq. Id. No. 5) (Cy3)-CAAAGCCTGGCATAA—N

Figure 13

SEQUENCE LISTING

<160> NUMBER OF SEQ ID NOS: 37

<210> SEQ ID NO 1
<211> LENGTH: 20
<212> TYPE: DNA
<213> ORGANISM: Homo sapiens

<400> SEQUENCE: 1
ccaacgtttc ggaccgtatt                                    20

<210> SEQ ID NO 2
<211> LENGTH: 40
<212> TYPE: RNA
<213> ORGANISM: Homo sapiens

<400> SEQUENCE: 2
cuuguacaga aauacggucc gaaaccaacc ucuguuauug               40

```
<210> SEQ ID NO 3
<211> LENGTH: 25
<212> TYPE: DNA
<213> ORGANISM: Homo sapiens

<400> SEQUENCE: 3
dgaaggtcga acaggaaggt tatct                                               25

<210> SEQ ID NO 4
<211> LENGTH: 15
<212> TYPE: DNA
<213> ORGANISM: Homo sapiens

<400> SEQUENCE: 4
ctttcggacc gtatt                                                          15

<210> SEQ ID NO 5
<211> LENGTH: 15
<212> TYPE: DNA
<213> ORGANISM: Homo sapiens

<400> SEQUENCE: 5
caaagcctgg cataa                                                          15

<210> SEQ ID NO 6
<211> LENGTH: 24
<212> TYPE: DNA
<213> ORGANISM: Homo sapiens

<400> SEQUENCE: 6
dgtaacgcta cagggtatgg aaca                                                24

<210> SEQ ID NO 7
<211> LENGTH: 24
<212> TYPE: DNA
<213> ORGANISM: Homo sapiens

<400> SEQUENCE: 7
tcaaaagcca gccagccagc agtg                                                24

<210> SEQ ID NO 8
<211> LENGTH: 21
<212> TYPE: DNA
<213> ORGANISM: Homo sapiens

<400> SEQUENCE: 8
gacagtcagc cgcatcttct t                                                   21

<210> SEQ ID NO 9
<211> LENGTH: 23
<212> TYPE: DNA
<213> ORGANISM: Homo sapiens

<400> SEQUENCE: 9
ccaatacgac caaatccgtt gac                                                 23

<210> SEQ ID NO 10
<211> LENGTH: 22
<212> TYPE: DNA
<213> ORGANISM: Homo sapiens

<400> SEQUENCE: 10
cgtcgccagc cgagccacat cg                                                  22
```

```
<210> SEQ ID NO 11
<211> LENGTH: 20
<212> TYPE: DNA
<213> ORGANISM: Homo sapiens

<400> SEQUENCE: 11
ccaacgtttc ggaccgtatt                                                   20

<210> SEQ ID NO 12
<211> LENGTH: 20
<212> TYPE: DNA
<213> ORGANISM: Homo sapiens

<400> SEQUENCE: 12
ccaacgtttc ggaccgtatt                                                   20

<210> SEQ ID NO 13
<211> LENGTH: 20
<212> TYPE: DNA
<213> ORGANISM: Homo sapiens

<400> SEQUENCE: 13
gaatgtgaca tttcgacacg                                                   20

<210> SEQ ID NO 14
<211> LENGTH: 20
<212> TYPE: DNA
<213> ORGANISM: Homo sapiens

<400> SEQUENCE: 14
aatacggtcc gaggtaccaa                                                   20

<210> SEQ ID NO 15
<211> LENGTH: 15
<212> TYPE: RNA
<213> ORGANISM: Homo sapiens

<400> SEQUENCE: 15 aauacgqucc gaaac                                                        15

<210> SEQ ID NO 16
<211> LENGTH: 20
<212> TYPE: RNA
<213> ORGANISM: Homo sapiens

<400> SEQUENCE: 16
aauacggucc gaaacguugg                                                   20

<210> SEQ ID NO 17
<211> LENGTH: 40
<212> TYPE: RNA
<213> ORGANISM: Homo sapiens

<400> SEQUENCE: 17
cuuguacaga aauacggucc gaaacguugg ucuguuauug                             40

<210> SEQ ID NO 18
<211> LENGTH: 20
<212> TYPE: DNA
<213> ORGANISM: Homo sapiens

<400> SEQUENCE: 18
```
aatacggtcc gaggtaccaa                                            20

<210> SEQ ID NO 19
<211> LENGTH: 20
<212> TYPE: DNA
<213> ORGANISM: Homo sapiens

<400> SEQUENCE: 19
aatacggtcc gaggtaccaa                                            20

<210> SEQ ID NO 20
<211> LENGTH: 20
<212> TYPE: DNA
<213> ORGANISM: Homo sapiens

<400> SEQUENCE: 20
aatacggtcc gaggtaccaa                                            20

<210> SEQ ID NO 21
<211> LENGTH: 20
<212> TYPE: DNA
<213> ORGANISM: Homo sapiens

<400> SEQUENCE: 21
aatacggtcc gaaacgccaa                                            20

<210> SEQ ID NO 22
<211> LENGTH: 18
<212> TYPE: DNA
<213> ORGANISM: Homo sapiens

<400> SEQUENCE: 22
aatacgtcca aacgttgg                                              18

<210> SEQ ID NO 23
<211> LENGTH: 20
<212> TYPE: DNA
<213> ORGANISM: Homo sapiens

<400> SEQUENCE: 23
ccaacgtttc ggaccgtatt                                            20

<210> SEQ ID NO 24
<211> LENGTH: 20
<212> TYPE: DNA
<213> ORGANISM: Homo sapiens

<400> SEQUENCE: 24
ccaacgtttc ggaccgtatt                                            20

<210> SEQ ID NO 25
<211> LENGTH: 20
<212> TYPE: DNA
<213> ORGANISM: Homo sapiens

<400> SEQUENCE: 25
aataccgtcc caaacgccaa                                            20

<210> SEQ ID NO 26
<211> LENGTH: 40
<212> TYPE: RNA
<213> ORGANISM: Homo sapiens

<400> SEQUENCE: 26
cuuguacaga aauacggucc gaaacguugg ucuguuauug         40

<210> SEQ ID NO 27
<211> LENGTH: 15
<212> TYPE: DNA
<213> ORGANISM: Homo sapiens

<400> SEQUENCE: 27
gtttcggacc gtatt                                    15

<210> SEQ ID NO 28
<211> LENGTH: 12
<212> TYPE: RNA
<213> ORGANISM: Homo sapiens

<400> SEQUENCE: 28
gucggggagg ua                                       12

<210> SEQ ID NO 29
<211> LENGTH: 18
<212> TYPE: RNA
<213> ORGANISM: Homo sapiens

<400> SEQUENCE: 29
uaccuccccg acgacacc                                 18

<210> SEQ ID NO 30
<211> LENGTH: 28
<212> TYPE: DNA
<213> ORGANISM: Homo sapiens

<400> SEQUENCE: 30
cagcgatgga ggggctgctg tggcgctg                      28

<210> SEQ ID NO 31
<211> LENGTH: 18
<212> TYPE: DNA
<213> ORGANISM: Homo sapiens

<400> SEQUENCE: 31
ccacagcagc ccctccat                                 18

<210> SEQ ID NO 32
<211> LENGTH: 12
<212> TYPE: DNA
<213> ORGANISM: Homo sapiens

<400> SEQUENCE: 32
atggaggggc tg                                       12

<210> SEQ ID NO 33
<211> LENGTH: 20
<212> TYPE: DNA
<213> ORGANISM: Homo sapiens

<400> SEQUENCE: 33
ttatgccagg ctttgcaacc                               20

<210> SEQ ID NO 34
<211> LENGTH: 20
<212> TYPE: DNA
<213> ORGANISM: Homo sapiens

```
<400> SEQUENCE: 34
ccaacgtttc ggaccgtatt                                              20

<210> SEQ ID NO 35
<211> LENGTH: 19
<212> TYPE: DNA
<213> ORGANISM: Homo sapiens

<400> SEQUENCE: 35
aatacgtccc aaacgttgg                                               19

<210> SEQ ID NO 36
<211> LENGTH: 20
<212> TYPE: DNA
<213> ORGANISM: Homo sapiens

<400> SEQUENCE: 36
aataccgtcc caggtaccaa                                              20

<210> SEQ ID NO 37
<211> LENGTH: 15
<212> TYPE: DNA
<213> ORGANISM: Homo sapiens

<400> SEQUENCE: 37
aatacggtcc gaaac                                                   15
```

PHOTOCLEAVABLE OLIGONUCLEOTIDE AND USES THEREOF

CROSS-REFERENCE TO RELATED APPLICATIONS

This application claims priority from U.S. Provisional Application Ser. No. 60/861,087, filed Nov. 27, 2006, and U.S. Provisional Application Ser. No. 60/881,165, filed Jan. 19, 2007, both which are incorporated herein by reference in their entirety.

FIELD OF INVENTION

This invention is directed to methods and compositions of oligonucleotide constructs having a photocleavable linker. Specifically, provided herein are methods and compositions utilizing a photocleavable linker, which when exposed to light modulates the expression of genes.

BACKGROUND OF THE INVENTION

Many gene silencing technologies have focused on targeting mRNA using ribozymes, DNAzymes, complementary RNA or DNA oligonucleotides. It is attractive that mRNA is accessible during transcription, processing (e.g., 5'-capping, intro-exon splicing, polyadenylation, nuclear export), and ribosomal binding and translation. Hybridization of an 'antisense' oligodeoxynucleotide (asODN) to a target mRNA inhibits translation by sterically blocking the ribosome and/or recruiting endogenous ribonucleases. In mammalian cells, mRNA/asODN duplex formation activates RNase H-mediated hydrolysis of mRNA. asODNs have proven effective in gene silencing in many experimental systems, and are being evaluated as treatments for cancer and other diseases in human clinical trials. It was recently reported that the stability of DNA hairpins relative to their corresponding RNA/DNA hybrids influenced the extent of RNA degradation by RNase H. Antisense peptide nucleic acids (PNAs) or DNA oligonucleotides with a morpholine backbone, down-regulate gene expression in many model organisms (such as fish, flies, frogs, chickens, worms, sea urchins) by sterically blocking ribosomal protein synthesis.

SUMMARY OF THE INVENTION

In one embodiment, provided herein is a photoactive oligonucleotide conjugate having the structure

X-Y-Z wherein X is an antisense oligonucleotide (asODN); Z is a sense oligonucleotide (sODN); and Y is a photocleavable linker covalently attached therebetween.

In another embodiment, provided herein is method of modulating RNA hydrolysis by RNase H, comprising the step of: contacting a RNA strand with a photocleavable oligonucleotide conjugate comprising a DNA, a phosphorothioated DNA (PS-DNA), or similar DNA strand, said conjugate comprising an antisense oligonucleotide, a sense oligonucleotide, and a photocleavable linker covalently attached therebetween; cleaving the conjugate with light; hybridizing the antisense oligonucleotide to its target RNA sequence; and digesting the hybridized oligonucleotide target RNA with RNase H, whereby the difference in the melting temperature ($\Delta T_m$) of the duplex formed between the antisense and sense oligonucleotide strands, before and after the step of photocleavage, modulates asDNA/RNA hybridization, and therefore the activity of RNase H.

In one embodiment, provided herein is a method of sterically blocking binding by a ribosome to a target mRNA, comprising the step of: contacting a RNA strand with a photocleavable oligonucleotide conjugate comprising a RNA, a PS-DNA, or similar DNA strand, said conjugate comprising an antisense oligonucleotide (asODN) capable of sterically blocking synthesis by a ribosome; a sense oligonucleotide; and a photocleavable linker covalently attached therebetween; cleaving the conjugate; hybridizing the antisense oligonucleotide to its target RNA sequence, whereby the difference in the melting temperature ($\Delta T_m$) of the duplex formed between the antisense and sense oligonucleotide strands, before and after the step of photocleavage, modulates asODN/RNA hybridization, and thereby controls ribosome binding.

In one embodiment, provided herein is a method of producing a heterobifunctional photocleavable linker, comprising the steps of: reacting maleimide with a furan, thereby obtaining 3,6-endoxo-$\Delta^4$-tetrahydrophthalimide; reacting 3,6-endoxo-$\Delta^4$-tetrahydrophthalimide and 1-(5-bromomethyl-2-nitrophenyl)-ethanol dissolved in anhydrous DMF with potassium carbonate, thereby creating 1-(5-(N-maleimidomethyl)-2-nitro-phenyl)ethanol; and reacting the obtained 1-(5-(N-maleimidomethyl)-2-nitro-phenyl)ethanol, DCC and trimethylamine, thereby obtaining a 1-(5-(N-maleimidomethyl)-2-nitro-phenyl)ethanol NHS ester mixture.

In another embodiment, provided herein is a method of manufacturing a photocleavable DNA oligonucleotide conjugate comprising the steps of: dissolving an antisense oligodeoxynucleotide (asODN) in a buffer, whereby the asODN comprises an unprotected thiol group; reacting a sense oligodeoxynucleotide with a photocleavable linker, whereby the sense oligodeoxynucleotide is no less than 85% complementary to the dissolved antisense oligodeoxynucleotide and the photocleavable linker comprises a thiol reactive group; reacting the antisense oligodeoxynucleotide comprising a free thiol group and sense oligodeoxynucleotide with the thiol-reactive photocleavable linker, thereby obtaining an antisense oligodeoxynucleotide—photocleavable linker—sense oligodeoxynucleotide conjugate; purifying the conjugate using reverse-phase and ion exchange HPLC chromatography, thereby obtaining a pure photocleavable DNA conjugate.

In one embodiment, provided herein is a method of reducing expression of a gene of interest in a subject, comprising contacting a cell comprising the gene of interest with a photocleavable conjugate, wherein the conjugate comprises an antisense oligodeoxynucleotide (asODN) having no less than 85% complementarity to the gene of interest, a sense strand complementary to said asODN, and a photocleavable linker attached therebetween; exposing the conjugate to an electromagnetic energy source, thereby cleaving the photocleavable linker; and reacting the asODN with the gene of interest.

In another embodiment, provided herein is a composition comprising: an antisense oligodeoxynucleotide (asODN) comprising a free thiol group; a sense oligodeoxynucleotide (sODN) complementary to said asODN; and a heterobifunctional photocleavable linker capable of being operably linked to the antisense oligodeoxynucleotide and to the sense oligodeoxynucleotide, to produce a photocleavable DNA conjugate.

In one embodiment, provided herein is a method of modulating the binding of an antisense molecule to mRNA, comprising the step of contacting the mRNA with a photocleavable oligonucleotide conjugate; cleaving the conjugate wherein the conjugate comprises an antisense oligodeoxynucleotide (asODN) complementary to the mRNA, a sense strand complementary to said asODN and a photocleavable linker attached therebetween; and exposing the conjugate to an electromagnetic energy source, thereby activating the asODN; and hybridizing the antisense oligonucleotide to the target mRNA.

In another embodiment, provided herein is a composition for reducing expression of a gene of interest in a subject comprising a photocleavable conjugate, wherein the conjugate comprises an antisense oligodeoxynucleotide (asODN) having no less than 85% complementarity to the gene of interest, a sense strand (sODN), complementary to said asODN, and a photocleavable linker attached therebetween; and wherein cleaving the photocleavable linker of the conjugate activates the asODN to react with the gene of interest.

In one embodiment, provided herein is an assay for determining the ability of a candidate nucleotide sequence to reduce expression of a gene of interest comprising the steps of contacting the gene of interest with a hairpin conjugate comprising the candidate nucleotide sequence, a blocking sequence complementary to the candidate nucleotide sequence and a photocleavable linker operably linked to the candidate nucleotide sequence and the blocking sequence; cleaving the conjugate; and analyzing the expression of the gene of interest, its regulated genes or the gene's or regulated genes' encoded proteins, whereby cleaving the photocleavable linker results in separating the candidate nucleotide sequence from the blocking sequence.

BRIEF DESCRIPTION OF THE DRAWINGS

FIG. 13 shows a 15-mer antisense S-DNA (top) attached via the PL to 15-mer sense S-DNA.

DETAILED DESCRIPTION OF THE INVENTION

Figure 1:
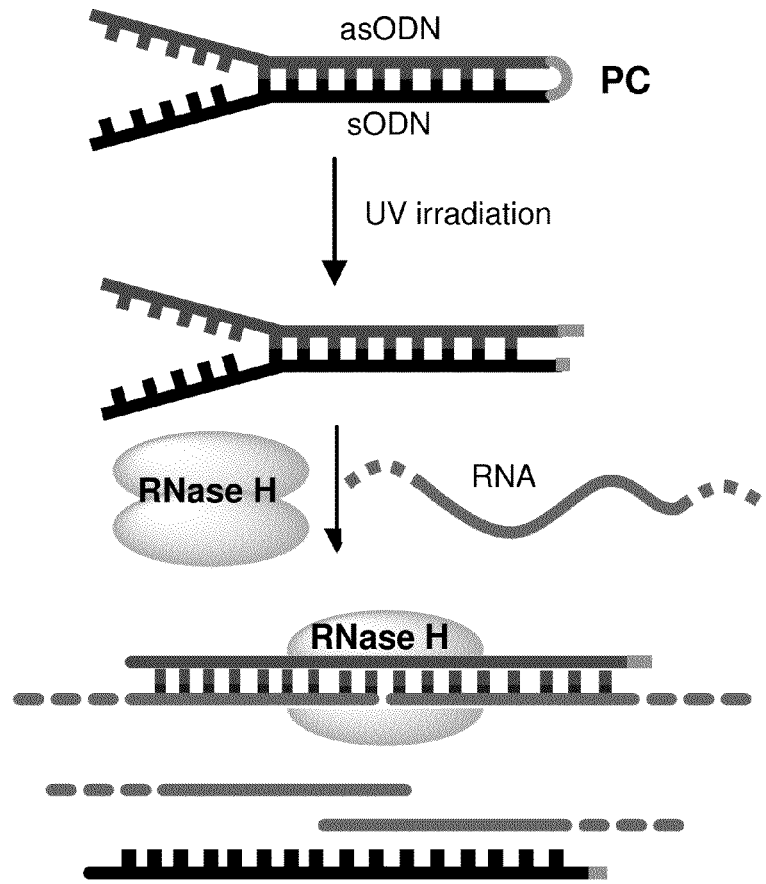
FIG. 1 shows A) Strategy for regulating RNA digestion by RNase H using a light-activated DNA hairpin. B) Sequences of the asODN-ODN conjugate and RNA targets; structure of the heterobifunctional photocleavable linker, PC. Underlined bases in RNA-40 are identical to RNA-20.
Figure 1:
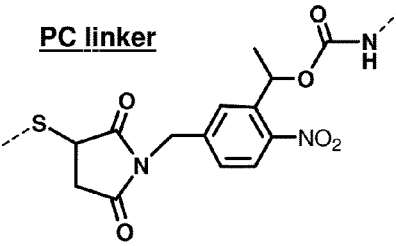

This invention relates in one embodiment to methods and compositions of oligonucletide constructs having a photocleavable linker operably linked thereto.

In one embodiment, a DNA hairpin is provided herein, which efficiently regulates DNA/DNA and DNA/RNA duplex formation using a single photoactive group. The stability of the DNA hairpin in one embodiment, or proper complementarity of the blocking group, and RNA structure in other embodiments, were important factors affecting RNA hydrolysis by RNase H. The methods and compositions provided herein represent in one embodiment an efficient method for photo-modulating this enzyme activity. Oligonucleotide conjugates as provided herein can be designed in one embodiment, to photo-regulate many other processes for biotechnological and cellular applications.

Therefore, provided herein is a photoactive oligonucleotide conjugate having the structure

X-Y-Z wherein X is an antisense oligonucleotide (asODN); Z is a sense oligonucleotide (sODN); and Y is a photocleavable linker covalently attached therebetween.

The term "nucleic acid" or "oligonucleotide" refers in one embodiment to a polymer or oligomer composed of nucleotide units (ribonucleotides, deoxyribonucleotides or related structural variants or synthetic analogs thereof) linked via phosphodiester bonds (or related structural variants or synthetic analogs thereof). Thus, the term refers to a nucleotide polymer in which the nucleotides and the linkages between them are naturally occurring (DNA or RNA), as well as various analogs, for example and without limitation, peptide nucleic acids (PNAs), phosphoramidates, phosphorothioates, methyl phosphonates, 2'-O-methyl ribonucleic acids, and the like. In one embodiment, the asODNs used in the compositions and methods provided herein, are nucleic acid sequences.

In one embodiment, the oligonucleotides used in the methods and compositions described herein, are synthetic peptide nucleic acids (PNAs) or negatively charged peptide nucleic acids (ncPNAs) which interact with the nucleotide sequence encoding a sequence of interest in a sequence-specific manner and silence function of a gene of interest. In another embodiment, the oligonucleotides used in the methods and compositions described herein, are locked nucleic acid (LNA), which interact with the nucleotide sequence encoding a sequence of interest, forming a LNA/DNA co-polymer, in a sequence-specific manner and substantially silence the function of a sequence of interest and its encoded protein. In one embodiment, the asODN used in the conjugates, compositions and methods described herein is asLNA.

Accordingly, in one embodiment, X comprises naturally occurring (DNA or RNA), as well as various analogs, or peptide nucleic acids (PNAs), phosphoramidates, phosphorothioates, methyl phosphonates, 2'-O-methyl ribonucleic acids, and the like in other embodiments. Likewise, and in another embodiment, Z will be selected to comprise an appropriate blocking nucleotide sequence, which may be in one embodiment naturally occurring (DNA or RNA), or various analogs, such as peptide-nucleic acids (PNAs), phosphoramidates, phosphorothioates, methyl phosphonates, 2'-O-methyl ribonucleic acids, and the like in other embodiments.

In another embodiment, the term "nucleotides" as used herein includes, but is not limited to, naturally occurring and/or synthetic nucleotides, nucleotide analogs, and nucleotide derivatives. For example, the term includes naturally occurring DNA or RNA monomers, nucleotides with backbone modifications such as peptide nucleic acid (PNA) (M. Egholm et al., Nature, 365, 566-568 (1993), incorporated by reference in its entirety), phosphorothioate DNA, phosphorodithioate DNA, phosphoramidate DNA, amide-linked DNA, MMI-linked DNA, 2'-O-methyl RNA, alpha-DNA and methylphosphonate DNA, nucleotides with sugar modifications such as 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-), inosine and diaminopurine.

In one embodiment oligomeric antisense compounds, particularly oligonucleotides, are used in the photocleavable hairpin oligonucleotide constructs provided herein. This is accomplished by providing antisense compounds which specifically hybridize with one or more sense ODN's as herein. As used herein, the terms "target nucleic acid" refers in one embodiment to RNA (including pre-mRNA and mRNA) transcribed from a DNA, and also cDNA derived from such RNA. The specific hybridization of an oligomeric compound with its target nucleic acid interferes in another embodiment, with the normal function of the nucleic acid. The modulation of function of a target nucleic acid by compounds which specifically hybridize to it, is referred to in one embodiment as "antisense". In one embodiment, the functions of DNA to be interfered with using the antisense oligonucleotides described herein, such as c-myb in one embodiment (see FIG. 12), which are used in the methods and compositions described herein, include replication and transcription. In another embodiment, functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the function of the target nucleic acid. In one embodiment, inhibition of gene expression is preferred and mRNA is a preferred target. In one embodiment, since many genes (including c-myb) have multiple transcripts, "inhibition" also includes an alteration in the ratio between gene products, such as alteration of mRNA splice products.

In one embodiment, specific nucleic acids are targeted for antisense. "Targeting" an antisense compound to a particular nucleic acid, in one embodiment, is a multi-step process. The process usually begins with the identification of a nucleic acid sequence whose function is to be inhibited. This may be, for example, a cellular gene (or mRNA transcribed from the gene) whose expression is associated with a particular disorder or disease state, or a nucleic acid molecule from an infectious agent. The targeting process also includes in another embodiment, determination of a site or sites within this gene for the antisense interaction to occur such that the desired effect, e.g., inhibition of expression of the protein such as chordin, will result. In one embodiment, an intragenic site is the region encompassing the translation initiation or termination codon of the open reading frame (ORF) of the gene. Since, the translation initiation codon is in one embodiment 5'-AUG (in transcribed mRNA molecules; 5'-ATG in the corresponding DNA molecule), the translation initiation codon is referred to in one embodiment as the "AUG codon," the "start codon" or the "AUG start codon". In another embodiment, a minority of genes have a translation initiation codon having the RNA sequence 5'-GUG, 5'-UUG or 5'-CUG, and 5'-AUA, 5'-ACG and 5'-CUG and have been shown to function in vivo. Thus, the terms "translation initiation codon" and "start codon" encompasses in other embodiments, many codon sequences, even though the initiator amino acid in each instance is typically methionine (in eukaryotes) or formylmethionine (in prokaryotes).

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be target regions in one embodiment, and are particularly useful in situations where aberrant splicing is implicated in disease, or where an overproduction of a particular mRNA splice product is implicated in disease in other embodiment, such as symptoms associated with HSV infection. Aberrant fusion junctions due to rearrangements or deletions are also preferred targets. In one embodiment, introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect. In one embodiment, the term "hybridization" refers to hydrogen bonding, which may be Watson-Crick, Hoogsteen or reversed Hoogsteen hydrogen bonding, between complementary nucleoside or nucleotide bases. In one embodiment, adenine and thymine are complementary nucleotide bases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are used in one embodiment, as research reagents and diagnostics. In another embodiment, antisense oligonucleotides, which are able to inhibit gene function, with extreme specificity, are used by those of ordinary skill to elucidate the function of particular genes. Antisense compounds are used in another embodiment, to distinguish between functions of various members of a biological pathway. Antisense modulation has, in one embodiment of the agents described in the methods and compositions described herein, been harnessed for research use.

Figure 15:
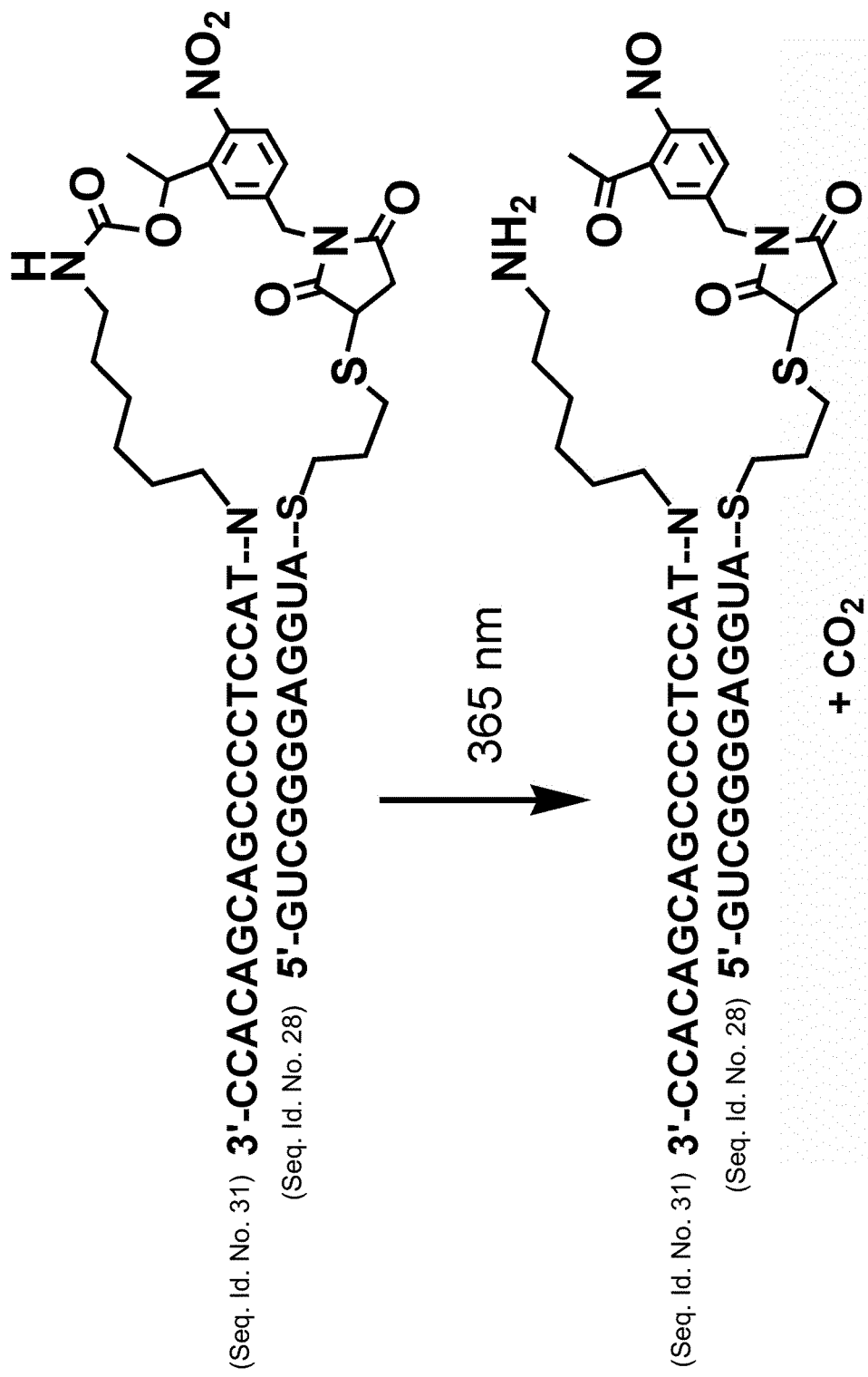
FIG. 15 shows a strategy for controlling gene expression using light-activated antisense peptide nucleic acid (asPNA) or antisense negatively charged peptide nucleic acid (ncPNA)
Figure 16:
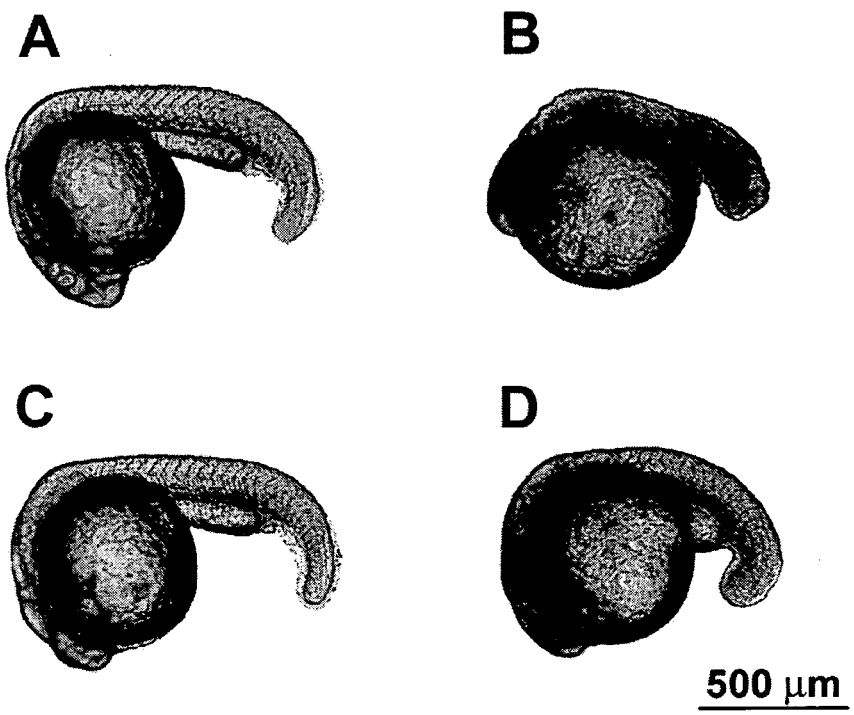
FIG. 16 shows transmitted light images of representative 24-hpf zebrafish embryos under different experimental conditions. A) Uninjected embryos were UV-irradiated at 3 hpf for 8 min and developed normally. B) Embryos were microinjected with asPNA and exhibited a strong 'no-chordin' phenotype. C) Embryos were injected with asPNA-PL-sRNA, and kept in the dark. Most embryos developed normally, as shown. D) Embryos injected with asPNA-PL-sRNA and UV-irradiated at 3 hpf showed a shortened tail, typical of chordin knockdown.

In one embodiment, the specificity and sensitivity of antisense agents described herein, is also harnessed for therapeutic uses. Antisense oligonucleotides are employed in one embodiment, as therapeutic moieties in the treatment of disease states in animals and man, such as, in another embodiment, those associated with cancer. In one embodiment, antisense oligonucleotides are safely and effectively administered to humans. In one embodiment oligonucleotides are useful therapeutic modalities that can be configured to be useful in treatment regimes of cells, tissues and animals, especially humans. Such configuration include inter-alia making the conjugates and compositions described herein, target c-myb and to be nuclease-resistant inside leukemia cells. (See FIG. 15.) In one embodiment, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, the term "locked nucleic acid" (LNA) refers to a synthetic nucleic acid analogue, incorporating "internally bridged" nucleoside analogues. Synthesis of LNA, and properties thereof, have been described by a number of authors: Nielsen et al, (1997 J. Chem. Soc. Perkin Trans. 1, 3423); Koshkin et al, (1998 Tetrahedron Letters 39, 4381); Singh & Wengel (1998 Chem. Commun. 1247); and Singh et al, (1998 Chem. Commun. 455). As with PNA, LNA exhibits greater thermal stability when paired with DNA, than do conventional DNA/DNA heteroduplexes. In one embodiment, LNA can be joined to DNA molecules by conventional techniques. Therefore, in one embodiment, LNA is to be preferred over PNA, for use in the agents of the methods and compositions described herein.

In one embodiment, the antisense oligonucleotide (asODN) used in the methods and compositions described herein, is between about 5 and 50 nucleotides in length. In another embodiment, the antisense oligonucleotide is between 5 and 10 nucleotides in length, or in another embodiment, the antisense oligonucleotide is between 5 and 15 nucleotides in length, or in another embodiment, the antisense oligonucleotide is between 5 and 20 nucleotides in length, or in another embodiment, the antisense oligonucleotide is between 5 and 25 nucleotides in length, or in another embodiment, the antisense oligonucleotide is between 5 and 30 nucleotides in length, or in another embodiment, the antisense oligonucleotide is between 5 and 35 nucleotides in length, or in another embodiment, the antisense oligonucleotide is between 5 and 40 nucleotides in length, or in another embodiment, the antisense oligonucleotide is between 5 and 45 nucleotides in length, or in another embodiment, the antisense oligonucleotide is between 5 and 49 nucleotides in length. In one embodiment, the antisense oligonucleotide (asODN) used in the methods and compositions described herein, is between about 10 and 20 nucleotides in length. In another embodiment, the antisense oligonucleotide is between 15 and 25 nucleotides in length, or in another embodiment, the antisense oligonucleotide is between 20 and 30 nucleotides in length, or in another embodiment, the antisense oligonucleotide is between 25 and 35 nucleotides in length.

In another embodiment, the 5' end of the antisense oligonucleotide and the 3' end of the sense oligonucleotide used in the methods and compositions described herein, each contain a region that is not complementary to the opposite strand. In one embodiment, having a non-complementary region in the sense or antisense ODNs used in the methods and compositions described herein, which is no less than 5 nucleotides in another embodiment, allows the design of the desired stability of the conjugate, by controlling the length of the complementary oligonucleotides. In one embodiment, the methods and compositions described herein, allow for the use of a 30-40 mer asODN with a much shorter sODN, thereby controlling the strength of interactions in the conjugate.

In another embodiment, the antisense or sense oligonucleotide used in the methods and compositions described herein, is a DNA peptide nucleic acid (PNA), phosphorothioate DNA, phosphorodithioate DNA, phosphoramidate DNA, amide-linked DNA, MMI-linked DNA, 2'-O-methyl RNA, alpha-DNA, methylphosphonate DNA, 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, anhydrohexitol DNA, C-5 substituted pyrimidine nucleoside, C-7 substituted 7-deazapurine nucleoside, inosine nucleoside phosphorodiamidate morpholino oligonucleotide (PMO), a locked nucleic acid (LNA) or diaminopurine nucleoside.

In one embodiment, the conjugate used in the compositions and methods described herein comprises the general structure of X-Y-Z, wherein X is antisense ncPNA; Z is 2'-O-methyl sRNA, comprising between about 10 to about 15 nucleotides and having a predetermined percent complementarity to X and Y, a photocleavable linker attached therebetween.

In one embodiment, the term "peptide nucleic acid (PNA)" refers to a polyglycine backbone, having purine and pyrimidine bases linked thereto by methylene carbonyl bonds. In one embodiment, since the backbone of PNA does not have any charged phosphate groups, the binding between asPNA/DNA strands used in the methods and compositions described herein, is stronger than between DNA/DNA strands due to the lack of electrostatic repulsion. In another embodiment, ncPNA does have alternating peptide and negatively charged phosphate groups. The negative charge makes the ncPNA more soluble than PNA.

Since, sDNA may prove to be toxic in certain applications, 2'-OMe sRNA may be selected as the blocking strand. In certain embodiments, the choice of sODN and asODN are optimized for the application for which they are used, and the skilled practitioner would readily recognize that experimentation as to the choice of reactive group (asODN) size and composition and the blocking group (sODN) size and composition, to optimize the functionality of the conjugate are well within the purview of due experimentation.

In another embodiment, locked nucleic acid (LNA) refers to a modified RNA nucleotide. Ribose moiety of LNA nucleotide is modified in one embodiment, with an extra bridge connecting 2' and 4' carbons. The bridge "locks" the ribose in the 3'-endo structural conformation, which is found in one embodiment, in A-form of DNA or RNA. LNA nucleotides may be mixed with DNA or RNA bases in the oligonucleotide in certain embodiments. The LNA oligonucleotides provided herein enhance base stacking and backbone pre-organization, which increases significantly the thermal stability (melting temperature) of the oligonucleotide conjugate.

In one embodiment, the term phosphorodiamidate morpholino oligonucleotide (PMO) refers to a synthetic polymorpholino backbone, to which nucleotide bases are linked through phosphorodiamidate groups. Like PNAs, PMOs do not have any charged phosphate groups, making the binding between asPMO/DNA strands used in the methods and compositions described herein, stronger than between DNA/DNA strands due to the lack of electrostatic repulsion. In certain embodiments, ncPNAs (unlike PMOs) do have charged phosphate groups, which is important for some applications.

In one embodiment, the photocleavable linker used in the methods and compositions described herein, is capable of reacting with thiol and amine functionalities. In one embodiment, the photocleavable linker (PL) can be positioned on either side of the duplex, with the asODN attached at either the 3' or 5' end, by either a thiol or amine functionality (see FIG. 13), thereby altering the stability and affinity of the asODN and increasing the versatility of the oligonucleotide conjugate. In one embodiment, the photocleavable linker used in the methods and compositions described herein, is 1-(5-(N-maleimidomethyl)-2-nitrophenyl)ethanol N-hydroxysuccinimide ester comprising in other embodiments a maleimido moiety, a N-hydroxysuccinimide ester moiety, or both.

In one embodiment, the photoactive oligonucleotide conjugates described hereinabove are used in the methods described herein.

In one embodiment, provided herein is a method of modulating RNA hydrolysis by RNase H, comprising the step of: contacting a RNA strand with a photocleavable oligonucleotide conjugate comprising a DNA, a PS-DNA, or similar DNA strand, said conjugate comprising an antisense oligonucleotide, a sense oligonucleotide, and a photocleavable linker covalently attached therebetween; cleaving the conjugate with light; hybridizing the antisense oligonucleotide to its target RNA sequence; and digesting the hybridized oligonucleotide target RNA with RNase H, whereby the difference in the melting temperature ($\Delta T_m$) of the duplex formed between the antisense and sense oligonucleotide strands, before and after the step of photocleavage, modulates asDNA/RNA hybridization, and therefore the activity of RNase H.

Ribonuclease H(RNase H) cleaves in one embodiment RNA of RNA-DNA hybrids in a sequence non-specific manner. RNase H comprises two classes (type 1/I and 2/II) based on amino acid sequence and biochemical properties. The principal mechanism by which antisense oligonucleotides affect the level of the target RNA is by activation of RNAse H, which cleaves the RNA strand of DNA/RNA hybrids. In certain embodiments, phosphodiester or phosphorothioate-linked DNA present in the photocleavable conjugates described herein activates endogenous RNAse H, thereby cleaving the targeted RNA. In one embodiment, phosphodiester-linked DNA is rapidly degraded by cellular nucleases and, with the exception of the phosphorothioate-linked DNA, nuclease resistant, non-naturally occurring DNA derivatives do not activate RNAse H when hybridized to RNA. In another embodiment, using PNA or LNA according to the methods and compositions described herein will ameliorate this circumstance.

In one embodiment, chimeric antisense oligos that have a short stretch of phosphorothioate DNA are used to obtain RNAse H-mediated cleavage of the target RNA. A minimum of 3 DNA bases is required in another embodiment, for activation of bacterial RNAse H or 5 bases are required for mammalian bacterial RNAse H activation. In one embodiment, the antisense oligonucleotide used in the conjugates and methods described herein, are between 3 and 50 nucleotides in length, or between 7 and 20 nucleotides in length in other embodiments.

In one embodiment, the antisense oligonucleotide used in the conjugates and methods described herein, is between 3 and 50, or between 3 and 40, or between 3 and 30, or between 3 and 20, or between 3 and 10, or between 5 and 15, or between 15 and 25, or between 10 and 35, or between 5 and 30, or between 10 and 20, or between 10 and 25, or between 15 and 25, or between 10 and 35, or between 10 and 50, or between 30 and 50 in other embodiments. In one embodiment, the antisense oligonucleotide used in the conjugates and methods described herein, is between 10 and 25, or between 3 and 15, or between 3 and 25, or between 3 and 35, or between 3 and 5, or between 5 and 10, or between 3 and 15, or between 3 and 25, or between 5 and 35, or between 10 and 35, or between 10 and 45, or between 15 and 20, or between 15 and 35, or between 10 and 45, or between 30 and 45 in other embodiments.

In one embodiment, provided herein is a method of sterically blocking ribosome binding to mRNA, comprising the step of: contacting a RNA strand with a photocleavable oligonucleotide conjugate comprising a RNA, a PS-DNA, or similar DNA strand, said conjugate comprising an antisense oligonucleotide (asODN) capable of sterically blocking binding by a ribosome; a sense oligonucleotide; and a photocleavable linker covalently attached therebetween; cleaving the conjugate; hybridizing the antisense oligonucleotide to its target RNA sequence, whereby the difference in the melting temperature ($\Delta T_m$) of the duplex formed between the antisense and sense oligonucleotide strands, before and after the step of photocleavage, modulates asDNA/RNA hybridization, and thereby sterically blocks the ribosome from binding.

In one embodiment, hybridization of asPNA or antisense ncPNA to an mRNA strand using the methods and compositions described herein, creates steric hindrance to binding of ribosomes to the target mRNA, thereby blocking the ability of the ribosome to synthesize the target mRNA-encoded proteins, effectively silencing the function of the gene encoding the mRNA.

Figure 14:
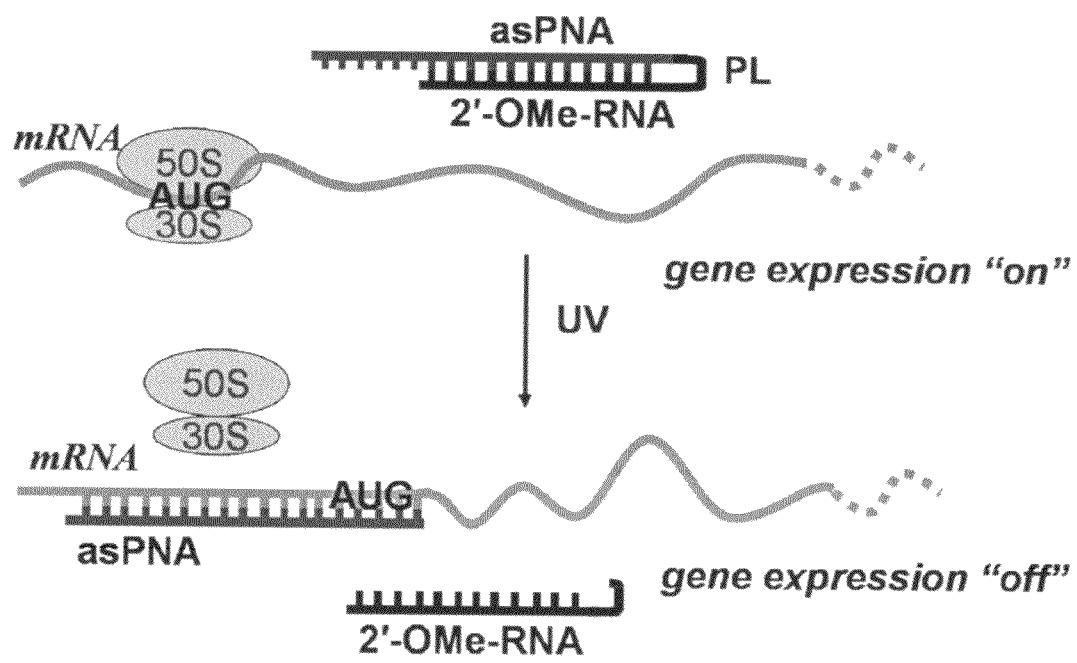
FIG. 14 shows antisense negatively charged PNA 18-mer targeting chordin (top strand, asPNA) is attached to sense 12-mer 2′-OMe RNA (bottom strand, sRNA) via a heterobifunctional photocleavable linker (PL). The asPNA-PL-sRNA conjugate is very stable ($T_m$~70° C.). Photoactivation at 365 nm yields the much less stable asPNA/sRNA duplex. In this form, the asPNA readily binds to complementary chordin mRNA, thereby blocking ribosomal protein synthesis.

In another embodiment, the photocleavable linker used in the conjugates and methods described herein is capable of reacting with —SH and —$NH_2$ functionalities of an oligonucleotide molecule. The skilled person would readily realize that the photocleavable linker (PL) can be positioned on either side of the conjugate (see FIG. 14), with the asODN attached at either the 3' or 5' end, and it can be attached in certain embodiments via either a thiol or amine functionality.

The "melting temperature" or "$T_m$" of double-stranded DNA, or RNA, or asODN-sODN used in the photocleavable conjugate described herein, refers in one embodiment to the temperature at which half of the structure of DNA, RNA, or asODN-sODN duplex is lost due to heating or other dissociation of the hydrogen bonding between base pairs, for example, by acid or alkali treatment, or the like. In one embodiment, the $T_m$ of a DNA molecule depends on its length and on its base composition. DNA molecules rich in GC base pairs have a higher $T_m$ than those having an abundance of AT base pairs. Separated complementary strands of DNA spontaneously re-associate or anneal in certain embodiments, to form duplex DNA when the temperature is lowered below the $T_m$. The highest rate of nucleic acid hybridization occurs in another embodiment 25° C. below the $T_m$. In one embodiment, contacting the photocleavable linker of the conjugate constructs described herein, in the methods described herein, lowers the $T_m$ of the conjugate, making the hybridization of the asODN with its target ssDNA or RNA more energetically preferable than reassociation with the sODN of the conjugate. In one embodiment, energetically preferable hybridization, refers to the circumstance whereby the differential in Gibbs free energy ($\Delta G$) associated with hybridization of the asODN with target DNA or RNA, is larger than the $\Delta G$ associated with the hybridization of the asODN with the sODN of the photoactivated conjugate.

The terms "hybridize" and "hybridization" refer in one embodiment, to the formation of complexes between nucleotide sequences which are sufficiently complementary to form complexes via Watson-Crick base pairing.

In one embodiment, the step of cleaving the photocleavable linker used in the conjugates and methods described herein, is obtained by contacting the oligonucleotide with electromagnetic radiation having a wavelength of between about 190 to about 2400 nm. In another embodiment, 1-(5-(N-maleimidomethyl)-2-nitro-phenyl)ethanol N-hydroxysuccinimide used in the conjugates and methods described herein results in breakage of the carbamate linkage upon UV illumination, resulting in lowering of the conjugate's $T_m$ and the asODN/ODN duplex becomes much less stable. In certain embodiments, the decrease in $T_m$ caused by contacting the photocleavable linker in the conjugates and methods described herein, is between about 20 to 30° C., or between about 10 to 30° C., or between about 20 to 40° C., or between about 15 to 35° C. in other embodiments.

The photo-modulation efficiency (i.e., the efficiency in reducing the stability of the conjugate), is controlled in one embodiment by the relative thermodynamic stabilities of the conjugate, pre- and post-photolysis, and the RNA-asODN duplexes. In another embodiments, the stability of the DNA conjugate, proper complementarity of the blocking group (sODN), and RNA structure are used in the methods described herein, for modulating RNA hydrolysis by RNase H. Optimization of these factors represents in one embodiment, the most efficient method for photo-modulating the enzyme activity of RNase H.

In one embodiment, the step of cleaving is obtained by contacting the oligonucleotide with electromagnetic radiation having a wavelength of between about 190 to about 2400 nm, or in another embodiment, between 196-720 nm, or in another embodiment, between 275-375 nm, or in another embodiment, between 520-720 nm. It would be readily recognized by the skilled person in the art, that the wavelength used in the methods described herein will vary with the application, the linker, the tissue and other similar factors wherein the conjugate is used, without changing the basic scope of the invention's embodiments described herein, namely that the cleaving of a single photolinker as described herein, destabilizes the conjugate, removing a blocking group of oligonucleotides from a reactive group of oligonucleotides, thereby making the latter reactive to the point where their hybridization with a target oligonucleotide sequence will be more energetically preferable, thereby activating in certain embodiments, RNase H, or reducing the expression of certain genes, their regulated genes or the functionality of the silenced genes' encoded proteins.

In certain embodiments, the photocleavable linker described hereinabove, is produced by the methods described herein. According to this aspect of the invention and in one embodiment, provided herein is a method of producing a heterobifunctional photocleavable linker, comprising the steps of: reacting maleimide with a furan, thereby obtaining 3,6-endoxo-$\Delta^4$-tetrahydrophthalimide; reacting 3,6-endoxo-$\Delta^4$-tetrahydrophthalimide and 1-(5-bromomethyl-2-nitrophenyl)-ethanol dissolved in anhydrous DMF with potassium carbonate, thereby creating 1-(5-(N-maleimidomethyl)-2-nitro-phenyl)ethanol; and reacting the obtained 1-(5-(N-maleimidomethyl)-2-nitro-phenyl)ethanol, DCC and trimethylamine, thereby obtaining a 1-(5-(N-maleimidomethyl)-2-nitro-phenyl)ethanol NHS ester mixture.

In another embodiment, the step of reacting 3,6-endoxo-$\Delta^4$-tetrahydrophthalimide and 1-(5-bromomethyl-2-nitrophenyl)-ethanol dissolved in anhydrous DMF with potassium carbonate in the method of producing a heterobifunctional photocleavable linker described herein, further comprises the steps of: diluting the solution with ethyl acetate and washing it with saturated NaCl solution; dehydrating the washed solution; concentrating the dehydrated solution thereby obtaining a crude product; dissolving the crude product in anisole; and removing the anisole, thereby creating a crude 1-(5-(N-maleimidomethyl)-2-nitro-phenyl)ethanol.

In one embodiment, the step of reacting the obtained 1-(5-(N-maleimidomethyl)-2-nitrophenyl)ethanol, DCC and trimethylamine in the method of producing a heterobifunctional photocleavable linker described herein, further comprises dissolving the reacting the obtained 1-(5-(N-maleimidomethyl)-2-nitrophenyl)ethanol and DCC in dry acetonitrile.

In another embodiment, the photocleavable linker described hereinabove, is used in the methods of producing the conjugates described herein.

In one embodiment, provided herein is a method of manufacturing a photocleavable DNA oligonucleotide conjugate comprising the steps of: dissolving an antisense oligodeoxynucleotide (asODN) in a buffer, whereby the asODN comprises in certain embodiments, an unprotected thiol group; reacting a sense oligo-deoxynucleotide with a photocleavable linker, whereby the sense oligodeoxynucleotide is no less than 85% complementary to the dissolved antisense oligodeoxynucleotide and the photocleavable linker comprises a thiol reactive group; reacting the antisense oligodeoxynucleotide comprising a free thiol group and sense oligodeoxynucleotide with the thiol-reactive photocleavable linker, thereby obtaining an antisense oligodeoxynucleotide—photocleavable linker—sense oligodeoxynucleotide conjugate; purifying the conjugate using reverse-phase or ion exchange HPLC chromatography, thereby obtaining a pure photocleavable DNA conjugate.

In one embodiment, the asODN used in the method of manufacturing a photocleavable DNA oligonucleotide conjugate, is complementary to a preselected target RNA, or DNA. In one embodiment, the asODN used in the methods and conjugates described herein, is sufficiently complementary to its target sequence. "Sufficiently complementary" refers in one embodiment to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, $2^{nd}$ ed. (Cold Spring Harbor Laboratory Press, Cold Spring Harbor, N.Y., 1989).

In one embodiment, minor groove-binding N-methylpyrrole (Py) and N-methylimidazole (Im) polyamides (peptides) uniquely recognize each of the four Watson-Crick base pairs. Antiparallel pairing of imidazole with pyrrole (Im/Py) recognizes in one embodiment, a G-C base pair, whereas in another embodiment, a Py/Py pair recognizes either an A-T or T-A base pair. The binding constant and sequence-specificity of the Py-Im hairpin polyamides are similar to that of a transcription factor. Therefore, many genes are silenced in other embodiments, by competitive binding of Py-Im hairpin polyamides to their regulatory sequences. Gene expression is controlled in one embodiment, by a combination of multiple common transcription factors. In one embodiment, inhibition of gene expression through the binding of Py-Im polyamides to regulatory sequences is unique to a specific gene, and contains part of the recognition sequence of the transcription factor together with the unique flanking sequences. In another embodiment, targeting Py-Im polyamide to the coding region is more straightforward when selecting a unique sequence.

In one embodiment, a homopyrimidine DNA strand (triplex forming oligonucleotide, TFO) can bind to a homopurine/homopyrimide DNA duplex in the major groove by forming Hoogsteen base pairs with the homopurine strand. The Hoogsteen base pairing scheme mediates sequence specific recognition of the double stranded DNA by the TFO where in one embodiment, an AT base pair is recognized by a T; and a GC base pair by a C that is protonated at N3+. In another embodiment, homopurine strands specifically form a DNA triplex in which the AT base pair is contacted by an A; and the GC base pair by a G. In one embodiment, the protected asODN component used in the conjugates and methods described herein, is a triplex forming oligonucleotide.

In one embodiment, the term "TFO" or "triplex forming oligonucleotide" refers to the synthetic oligonucleotides of the present invention which are capable of forming a triple helix by binding in the major groove with a duplex DNA structure.

In another embodiment, the term "bases" refers to both the deoxyribonucleic acids and ribonucleic acids. The following abbreviations are used, "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill in this art would readily recognize that these bases may be modified or derivatized to optimize the methods described herein, without changing the scope of the invention.

In one embodiment, provided herein is a photocleavable DNA conjugate produced by dissolving an antisense oligodeoxynucleotide (asODN) in a buffer, whereby the asODN comprises in certain embodiments, an unprotected thiol group; reacting a sense oligo-deoxynucleotide with a photocleavable linker, whereby the sense oligodeoxynucleotide is no less than 85% complementary to the dissolved antisense oligodeoxynucleotide and the photocleavable linker comprises a thiol reactive group; reacting the antisense oligodeoxynucleotide comprising a free thiol group and sense oligodeoxynucleotide with the thiol-reactive photocleavable linker, thereby obtaining an antisense oligodeoxynucleotide—photocleavable linker—sense oligodeoxynucleotide conjugate; purifying the conjugate using affinity chromatography, thereby obtaining a pure photocleavable DNA conjugate.

In another embodiment, the photocleavable linker used in the photocleavable DNA conjugate produced by dissolving an antisense oligodeoxynucleotide (asODN) in a buffer, whereby the asODN comprises in certain embodiments, an unprotected thiol group; reacting a sense oligo-deoxynucleotide with a photocleavable linker, whereby the sense oligodeoxynucleotide is no less than 85% complementary to the dissolved antisense oligo-deoxynucleotide and the photocleavable linker comprises a thiol reactive group; reacting the antisense oligodeoxynucleotide comprising a free thiol group and sense oligodeoxynucleotide with the thiol-reactive photocleavable linker, thereby obtaining an antisense oligodeoxynucleotide—photocleavable linker—sense oligodeoxynucleotide conjugate; purifying the conjugate using affinity chromatography, thereby obtaining a pure photocleavable DNA conjugate; is produced by reacting maleimide with a furan, thereby obtaining 3,6-endoxo-$\Delta^4$-tetrahydrophthalimide; reacting 3,6-endoxo-$\Delta^4$-tetrahydrophthalimide and 1-(5-bromomethyl-2-nitrophenyl)-ethanol dissolved in anhydrous DMF with potassium carbonate, thereby creating 1-(5-(N-maleimidomethyl)-2-nitro-phenyl)ethanol; and reacting the obtained 1-(5-(N-maleimidomethyl)-2-nitro-phenyl)ethanol, DCC and trimethylamine, thereby obtaining a 1-(5-(N-maleimidomethyl)-2-nitro-phenyl)ethanol NHS ester mixture.

In another embodiment, the asODN used in the photocleavable DNA conjugate produced by dissolving an antisense oligodeoxynucleotide (asODN) in a buffer, whereby the asODN comprises in certain embodiments, an unprotected thiol group; reacting a sense oligo-deoxynucleotide with a photocleavable linker, whereby the sense oligodeoxynucleotide is no less than 85% complementary to the dissolved antisense oligodeoxynucleotide and the photocleavable linker comprises a thiol reactive group; reacting the antisense oligodeoxynucleotide comprising a free thiol group and sense oligodeoxynucleotide with the thiol-reactive photocleavable linker, thereby obtaining an antisense oligodeoxynucleotide—photocleavable linker—sense oligodeoxynucleotide conjugate; purifying the conjugate using affinity chromatography, thereby obtaining a pure photocleavable DNA conjugate; has at least 85% homology to the sequence set forth in SEQ ID NO. 1 (CCAACGTTTCGG ACCGTATT), or in another embodiment or CTTTCGGACCGTATT (SEQ ID No. 4). In one embodiment the sODN comprises an oligooxynucleotide sequence having at least 85% homology to the sequence set for the in SEQ ID NO. 2 (CUU GUA CAG AAAUACGGUCCGAAACCA ACC UCU GUU AUU G). or CAAAGCCTGGCATAA (SEQ ID No.5).

In one embodiment, the asODN used in the photocleavable DNA conjugate produced by dissolving an antisense oligodeoxynucleotide (asODN) in a buffer, whereby the asODN comprises in certain embodiments, an unprotected thiol group; reacting a sense oligo-deoxynucleotide with a photocleavable linker, whereby the sense oligodeoxynucleotide is no less than 85% complementary to the dissolved antisense oligo-deoxynucleotide and the photocleavable linker comprises a thiol reactive group; reacting the antisense oligodeoxynucleotide comprising a free thiol group and sense oligodeoxynucleotide with the thiol-reactive photocleavable linker, thereby obtaining an antisense oligodeoxynucleotide—photocleavable linker—sense oligodeoxynucleotide conjugate; purifying the conjugate using reverse-phase or ion exchange HPLC chromatography, thereby obtaining a pure photocleavable DNA conjugate, which is an asPNA, or asLNA, asTFO, or asMorpholino in other embodiments. In one embodiment, the asPNA comprises between 10 and 20 nucleotides, or in another embodiment between about 3 to about 50 nucleotides.

In one embodiment, the conjugates, methods and photocleavable linkers described herein, are used in the methods of silencing genes' expression as described herein. According to this aspect of the invention, provided herein is a method of reducing expression of a gene of interest in a subject, comprising contacting a cell comprising the gene of interest with a photocleavable conjugate, wherein the conjugate comprises an antisense oligodeoxynucleotide (asODN) having no less than 85% complementarity to the gene of interest, a sense strand complementary to said asODN, and a photocleavable linker attached therebetween; exposing the conjugate to an electromagnetic energy source, thereby cleaving the conjugate; and reacting the asODN with the gene of interest.

In another embodiment, the asODN and the sense oligonucleotide (sODN) used in the methods of reducing expression of a gene of interest in a subject as described herein, are each independently DNA or PS-DNA, whereby the PC linker can attach to either the 3' end of the asODN and the 5' side of the sODN, or in another embodiment, to the 5' side of the asODN and the 3' side of the sODN. In one embodiment, the asODN is PNA and the sense strand is PNA, morpholine-based, DNA, or 2'-OMe RNA.

In one embodiment, the compositions described herein, are used to carry out the methods described herein. According to this aspect of the invention and in one embodiment, provided herein is a composition comprising an antisense oligodeoxynucleotide (asODN) comprising a free thiol group; a sense oligodeoxynucleotide (sODN) complementary to said asODN; and a heterobifunctional photocleavable linker, capable of being operably linked to the antisense oligodeoxynucleotide and to the sense oligodeoxynucleotide; to produce a photocleavable DNA conjugate, whereby in another embodiment, the photocleavable linker is capable of reacting with thiol and amine functionalities on the linker.

In another embodiment, provided herein is a composition for reducing expression of a gene of interest in a subject comprising a photocleavable conjugate, wherein the conjugate comprises an antisense oligodeoxynucleotide (asODN) having no less than 85% complementarity to the gene of interest, a sense strand (sODN), complementary to said asODN, and a photocleavable linker attached therebetween; and wherein cleaving the photocleavable linker of the conjugate activates the asODN to react with the gene of interest.

In one embodiment, the methods of producing the conjugates described herein, or the photocleavable linkers described herein, or both; are used in the compositions described herein. According to this aspect of the invention and in one embodiment, provided herein is a composition for reducing expression of a gene of interest in a subject comprising a photocleavable conjugate, wherein the conjugate comprises an antisense oligodeoxynucleotide (asODN) having no less than 85% complementarity to the gene of interest, a sense strand (sODN), complementary to said asODN, and a photocleavable linker attached therebetween; and wherein cleaving the photocleavable linker of the conjugate activates the asODN to react with the gene of interest.

In one embodiment, the compositions described hereinabove, are used in the methods described herein. According to this aspect of the invention and in one embodiment, provided herein is a method of modulating the binding of an antisense molecule to mRNA, comprising the step of contacting the mRNA with a photocleavable oligonucleotide conjugate; cleaving the conjugate wherein the conjugate comprises an antisense oligonucleotide (asODN) complementary to the mRNA target, a sense strand complementary to said asODN and a photocleavable linker attached therebetween; and contacting the conjugate with an electromagnetic energy source, thereby activating the asODN; and hybridizing the antisense oligonucleotide to the target mRNA. In one embodiment, the antisense oligonucleotide is an antisense peptide nucleic acid (asPNA). In another embodiment, the sense oligonucleotide (sODN) comprises a DNA, a peptide nucleic acid (PNA), a phosphorothioate DNA (PS-DNA), a phosphorodiamidate morpholino oligonucleotide (PMO), or a locked nucleic acid (LNA), or 2'-O-methyl RNA. (2'-OMe RNA) in other embodiments.

In one embodiment, the sense oligonucleotide (sODN) is a peptide nucleic acid (PNA), or in another embodiment the sense oligonucleotide (sODN) is a phosphorothioate DNA (PS-DNA), or in another embodiment the sense oligonucleotide (sODN) is a phosphorodiamidate morpholino oligonucleotide (PMO), or in another embodiment the sense oligonucleotide (sODN) is a locked nucleic acid (LNA), or in another embodiment the sense oligonucleotide (sODN) is 2'-O-methyl RNA. (2'-OMe RNA).

In one embodiment, the compositions and methods described herein are effective in controlling expression of developmentally important genes using a light-activated asPNA. The asPNA is transiently blocked in another embodiment, with a complementary 2'-OMe-RNA sense strand attached via a single photocleavable linker. UV light efficiently restores in certain embodiment antisense activity. In one embodiment, it is possible to vary protein levels quantitatively by photoregulating the concentration of active asPNA. In another embodiment, caged asPNAs are optimized for the photoregulation of several genes in vivo.

In another embodiment, photocleaved asPNA-PL-sRNA may remain hybridized after UV exposure, with an equilibrium between the asPNA/sRNA and asPNA/mRNA duplex forms. In certain embodiments, this binding competition lowers the effective concentration of asPNA that could bind mRNA and block translation, and are compensated for by increasing the dosage of the administered asPNA-PL-sRNA.

In another embodiment, provided herein is an assay for determining the ability of a candidate nucleotide sequence to reduce expression of a gene of interest comprising the steps of contacting the gene of interest with a hairpin conjugate comprising the candidate nucleotide sequence, a blocking sequence complimentary to the candidate nucleotide sequence and a photocleavable linker operably linked to the candidate nucleotide sequence and the blocking sequence; cleaving the conjugate; and analyzing the expression of the gene of interest, its regulated genes or the gene's or regulated genes' encoded proteins, whereby cleaving the photocleavable linker results in separating the candidate nucleotide sequence from the blocking sequence.

In one embodiment, maximizing activity and resistance to nucleases within the cell is enhanced considerably by modifying the backbone of the oligonucleotide of the compositions used in the methods described herein, as exemplified in one embodiment by phosphorothioate, or peptide, morpholine, and 'locked' nucleic acids in other discrete embodiments, as described herein. Thus, the methods described herein using the phosphorothioated DNA conjugates described herein in certain embodiments, for cellular studies is readily applied to the development of related antisense molecules for biotechnological and cellular applications.

In one embodiment, the methods described herein, using the compositions described herein are used for targeting a cancer-related gene using light-activated oligonucleotides. DNA conjugates are designed in another embodiment, to regulate DNA/DNA and DNA/RNA duplex formation using a single photoactive moiety. In one embodiment, down-regulation by more than two-fold of c-myb mRNA and c-MYB protein in human K562 (leukemia) is achieved using the conjugates described herein, In one embodiment, the conjugates described herein, which are used in the methods described are stabilized by smaller hairpin loops. In another embodiment the loop in the conjugates described herein, is formed by only the photocleavable linker, with no intervening oligonucleotides. In another embodiment, base pair mismatches have a large effect on destabilizing photoactive conjugates and related asODN/sODN duplexes. In one embodiment, stabilizing the conjugate used in the methods described herein, helps to minimize background RNA cleavage.

In one embodiment, a significant knockdown of c-myb mRNA (56%) and c-MYB protein is attained after photoactivation of S-C5. In another embodiment, the light-activated antisense molecules described herein, provides a versatile method for modulating the activity of RNase H. In one embodiment, using the methods described herein, light-activated oligonucleotides are readily adapted and applied to other biological processes that involve DNA/DNA, DNA/RNA, and RNA/RNA hybridization.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods

RNase Assays

The standard procedure for the RNase H assay was as follows: the DNA conjugate was annealed in the 1× ribonuclease H reaction buffer (20 mM Tris-HCl, 20 mM KCl, 10 mM $MgCl_2$, 0.1 mM EDTA, 0.1 mM DTT, pH 8.0) by heating to 95° C., slowly cooling to 70° C. and remaining at 70° C. for 10 min to melt non-specific DNA structures, then continuing slow cooling to 37° C. [γ-$^{32}$P]-labeled RNA oligonucleotide was added and incubated at 37° C. for 20 min to allow RNA/DNA duplex formation. RNase H was added to the mixture and incubated at 37° C. Total reaction volume was 10 μL and final concentrations of conjugate or control (asODN), and RNA (RNA-15, RNA-20, or RNA-40) were 0.01 μM and 2 μM, respectively. Time points were taken at 10 and 60 min by sampling 4 μL of the reaction mixture, adding 6 μl loading buffer (50 mM EDTA, 90% formamide), and heating to 95° C. for 3 min to terminate the reaction. Finally, 5 μL of the resulting solution was subject to electrophoresis on a polyacrylamide gel containing 7 M urea. RNA imaging was performed using a Storm phosphorimager and quantified with IMAGEQUANT software (Amersham Biosciences). To measure RNA degradation after photoactivation, the annealed DNA hairpin was illuminated (Xe lamp with monochromator, 355 nm, 36 mW/cm$^2$, 10 min) then [γ-$^{32}$P]-labeled RNA oligonucleotide was added and incubated for 20 min. RNA degradation by RNase H was determined as described above. See Supporting Information for synthetic details for the heterobifunctional photocleavable linker and conjugate, HPLC traces before and after photolysis of the conjugate, thermal denaturation methods, DNA and RNA melting curves, calculation of thermodynamic parameters, and gels of RNA digestion by RNase H.

Thermal Denaturation and Circular Dichroism Studies

Thermal denaturation studies were performed on conjugates in standard RNase H buffer. The concentration was determined by dissolving each conjugate in pure water and measuring the absorbance at 260 nm at 80° C. The solution was heated to 90° C. for 5 min, and allowed to cool gradually to 25° C. Samples were monitored at 260 nm while heating or cooling at a rate of 0.5° C./min. Melting temperatures were determined from the peak of the first derivative plot of $Abs_{260}$ vs. temperature.

CD spectra were collected on an Aviv 62DS spectropolarimeter in the wavelength range of 200-320 nm at 25° C. using a 1 mm quartz cell. Oligonucleotide solutions (conjugate or corresponding 1:1 asODN/sODN duplex) were 30 μM in 1× RNase H buffer.

Cell Culture and Transfection of Oligonucleotides

K562 cells (American Type Culture Collection, Manassas, Va., catalog no. CCL-243™) were cultured in RPMI 1640 supplemented with 10% fetal bovine serum (FBS) and 0.5% penicillin/streptomycin. The cells were maintained at 37° C. in a humidified incubator (95% humidity) and 5% $CO_2$. Culture media was changed every two days or according to the rapidity of cell growth.

Cells were transfected with ODNs using an Amaxa Nucleofector Kit (Amaxa, Inc., Gaithersburg, Md.) according to manufacturer's instructions. Typically, 3×10$^6$ cells were electroporated with 5 μg of ODN for each condition. The cells were first washed with phosphate buffered saline (PBS) and then resuspended in 100 μL of nucleofection solution. The ODN was added to the cell suspension which was then nucleofected using Program Q-29. Immediately after, the cells were transferred to 5 mL of culture medium and placed in the incubator. Three hours after nucleofection, one batch of cells was exposed to UV irradiation for 5 min by placing the 6-well plates (TPP 92406, Sigma) containing the cells on top of the illuminator. The plastic plates transmitted 70% of UV light at 360 nm, as determined by UV/Vis spectrometer. The cells in each well were then washed in PBS, and resuspended in 3 mL of culture media for 24 h.

Quantitative Real Time PCR (QRT-PCR)

Total RNA from cell pellets was isolated using RNeasy Mini Kit (Qiagen, Valencia, Calif.) according to the manufacturer's instructions. Reverse transcription was carried out with 1 μg RNA aliquots using iScript reverse transcription kit (Bio-Rad Laboratories, Hercules, Calif.). 1 μL cDNA was used as template for the QRT-PCR reaction. Taqman Universal PCR master mix (Applied Biosystems, Foster City, Calif.) was used for the PCR reaction and detection using iCycler iQ Real-Time PCR Detection System (BioRad). The assay was performed as in Kalota et al. (44) For amplifying c-myb product, the following primers were used: forward, dGAAGGTCGAACAGGAAGGTTATCT (SEQ ID No. 3); and reverse, dGTAACGCTACAGGGTATGGAACA (SEQ ID No. 6). The c-myb probe was labeled with 6-carboxyfluorescein (FAM) at the 5' end and Black Hole quencher (BHQ) at the 3' end. The probe sequence was 5'-TCAAAAGCCAGC-CAGCCAGCAGTG (SEQ ID No. 7).

GAPDH, a common housekeeping gene, was employed as a reference for QRT-PCR, and amplified with the following primers: forward, 5'-GACAGTCAGCCGCATCTTCTT (SEQ ID No. 8); and reverse, 5'-CCAATACGACCAAATC-CGTTGAC (SEQ ID No. 9). The GAPDH probe was labeled with FAM at 5' end and BHQ at 3' end. The probe sequence was 5'-CGTCGCCAGCCGAGCCACATCG (SEQ ID No. 10).

All reactions were performed in triplicate with 1 μL cDNA. The volume of reaction mixture was 15 μL. The reaction mixture was pre-incubated at 50° C. for 2 min. PCR cycling conditions were as follows: denaturation at 95° C. for 10 min, followed by 39 cycles of 92° C. for 15 s and 60° C. for 45 s. Analysis of QRT-PCR data was based on comparison of the target transcript PCR signal in a treatment group to signal measured in an untreated control. Analysis was done using the 2$^{-\Delta\Delta CT}$ method as described by Livak and Schmittgen [Livak, K. J. and Schmittgen, T. D. (2001) Analysis of relative gene expression data using real-time quantitative PCR and the 2 CT method. Methods, 25, 402-408.].

Protein Isolation and Western Blotting 24 h after nucleofection, cells were harvested, washed in PBS and pelleted. The cell pellets were lysed using 50 μL Triple-Lysis Buffer (50 mM TRIS, 150 mM NaCl, 0.02% sodium azide, 0.1% SDS and 1% Igepal; Sigma, St. Louis, Mo.) by incubating on ice for 30 min with vortexing every 10 min. The cell lysates were spun at maximum speed in a microfuge at 4° C. for 20 min. The supernatant thus extracted was used for western blotting.

Protein concentration in each sample was measured using a Bradford protein assay (Bio-Rad). Samples (100 µg) were loaded onto a 10% polyacrylamide gel (100 V, 90 min), then transferred to a PVDF membrane (20 V, 60 min) using a semi-dry blotting system (Bio-Rad). A 5% solution of non-fat dry milk was used as a blocking reagent. The membrane was incubated overnight at 4° C. with primary antibody against c-MYB (clone 1-1 from Upstate, Lake Placid, N.Y.) at 1:1000 dilution. The membrane was washed with TBS-T three times and probed with HRP-conjugated anti-mouse secondary antibody (GE Healthcare, UK) at 1:1000 dilution at room temperature for 1 h. Blots were developed using enhanced chemiluminescence ECL+ western blotting detection kit (GE Healthcare, UK). Membranes were then stripped using Re-Blot stripping solution (Chemicon, Temecula, Calif.) for 10 min at rt. After blocking, the membrane was incubated with anti-GAPDH antibody (Cell Signaling Technology, Inc., Danvers, Mass.) overnight at 4° C. at 1:1000 dilution, washed in PBS and then incubated with HRP-conjugated anti-rabbit secondary antibody (GE Healthcare, UK). Chemiluminescence was detected using the ECL kit (GE Healthcare, UK). Quantification of the bands was carried out using ImageQuant.

Example 1

Photocleavable Oligonucletide Construction

A light-activated DNA hairpin was synthesized by covalently attaching a 20-mer asODN to an ODN with 12 complementary bases via a heterobifunctional photocleavable linker (PC, FIG. 1). This 1-(5-(N-maleimidomethyl)-2-nitro-phenyl)ethanol N-hydroxysuccinimide ester was designed to react with thiol and amine functionalities on opposite ends of the linker (FIG. 1B). PC was synthesized in four steps in 14% yield. Its dual reactivity made it even more versatile for bioconjugation reactions than the 1-[5-(aminomethyl)-2-nitrophenyl]ethanol linker used previously. Covalent attachments of the thiolated asODN to the maleimido group and the amino-ODN to the N-hydroxysuccinimide ester occurred in good yields. Purification of the conjugated DNA hairpin was achieved by ion exchange chromatography at 40° C. This step was particularly important because any unreacted asODN would readily form a duplex with the target RNA, and promote RNase H activity.

Example 2

Photocleavable Linker Exposure to Light Activates asODN by Reducing $T_m$

The DNA hairpin exhibited a high melting temperature, $T_m$=80° C. Upon UV illumination, the carbamate linkage was broken and the asODN/ODN duplex became much less stable, $T_m$=51° C. Photocleavage was confirmed by HPLC and MALDI-TOF mass spectrometry. This large difference in thermal stability, $\Delta T_m$=29° C., allowed the photo-modulation of RNA/asODN duplex formation, thereby regulating RNA hydrolysis by RNase H (FIG. 1A).

Example 3

Photocleavable Oligonucleotide Construct Modulates Rnase H Activity

Figure 2:
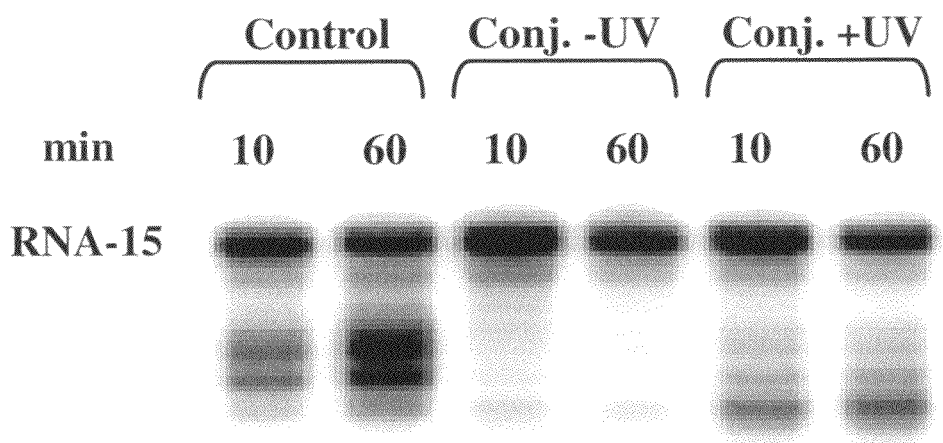
FIG. 2 shows denaturing PAGE (20%) analysis of RNA-15 digestion by RNase H at 37° C. Lanes 1-2, asODN; Lanes 3-4, conjugate (conj. −UV); Lanes 5-6, UV-activated conjugate (conj. +UV)

RNase H activity was studied with RNA oligomers of varied length, RNA-15 (15-mer), RNA-20 (20-mer) and RNA-40 (40-mer). Digestion of each RNA target was compared between solutions containing the control single-stranded asODN (CCAACGTTTCGG ACCGTATT, SEQ ID NO. 1) or the DNA hairpin. FIG. 2 shows hydrolysis of 45% of the total RNA-15 target after photoactivation, as compared to only 4.6% for the conjugate in a 1-h experiment with 1 unit of enzyme. Under the same conditions, 66% RNA degradation for the control single-stranded asODN was observed. The UV light used in these experiments had no effect on the enzyme or RNA stability. Control experiments confirmed that RNase H hydrolyzed RNA only when hybridized with asODN.

Figure 3:
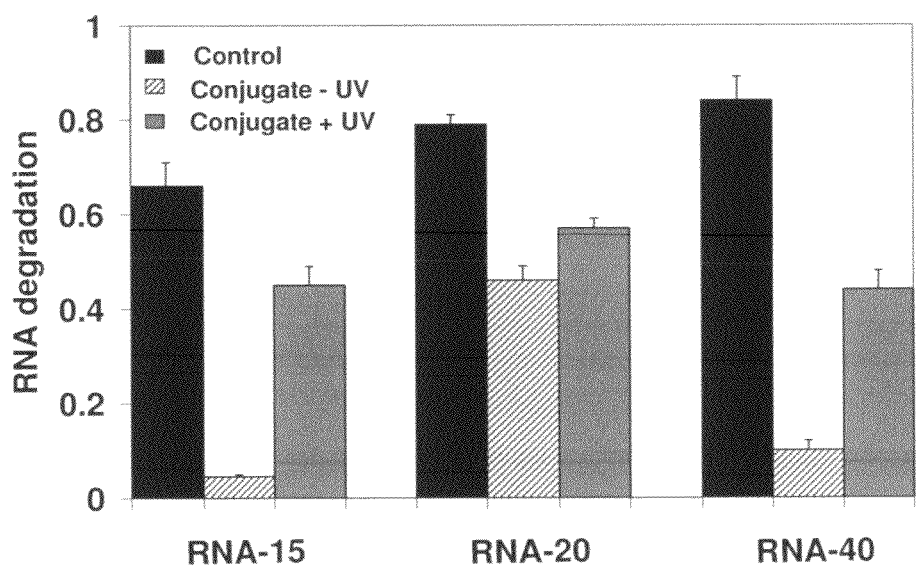
FIG. 3 shows RNase H assays showing degradation of RNA-15, RNA-20, and RNA-40 target sequences in 60 min at 37° C. with 1 unit of RNase H. Error bars signify the variation from two separate trials. The control lanes show hydrolysis of RNA hybridized to asODN.
Figure 4:
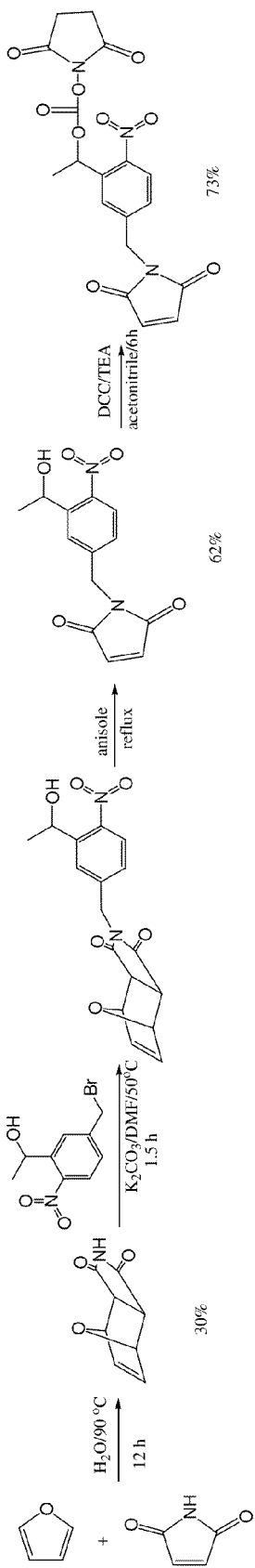
FIG. 4 shows a schematic of the synthesis of heterobifunctional photocleavable linker, PC.
Figure 5:
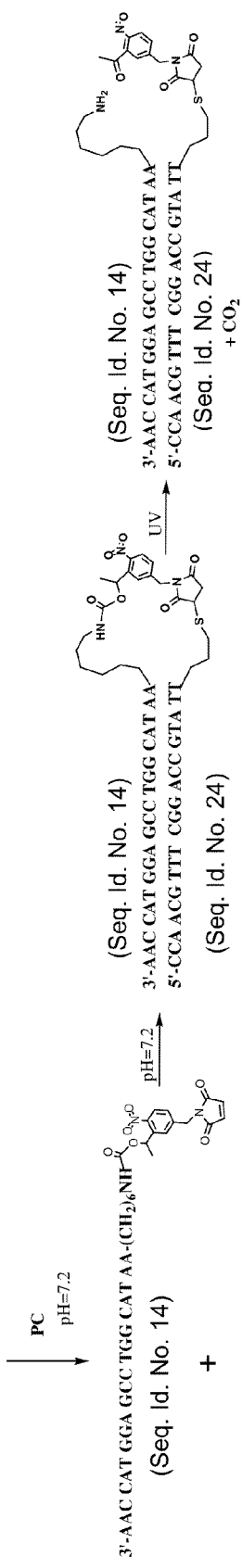
FIG. 5 shows a schematic of the synthesis of conjugate and UV-mediated photochemical reaction.

RNase H assays were also performed with RNA-20 and RNA-40. After photolysis of the DNA hairpin, RNA-20 and RNA-40 digestion increased by a factor of 1.3±0.2 and 4.4±0.4 versus a 9.0±1.0-fold increase for RNA-15 (FIG. 3). Three units of fresh RNase H gave nearly complete digestion of RNA-15 (98%), RNA-20 (88%) and RNA-40 (84%) in 1 h in the presence of the control asODN or photolyzed conjugate. This compared favorably to the consumption of only 49% of RNA-15, 70% of RNA-20 and 27% of RNA-40 using the DNA hairpin. RNA-40 is more representative of cellular mRNA, which has secondary structure that can limit nonspecific DNA hybridization and RNase H digestion. Within a cell, where an mRNA molecule can template the synthesis of several thousand proteins per hour, the ability to photo-modulate target mRNA between 73% and 16% of basal levels, as was shown for RNA-40, would produce a large effect.

The observed photo-modulation efficiency was controlled predominantly by the relative thermodynamic stabilities of the conjugate, pre- and post-photolysis, and the RNA-asODN duplexes. The melting temperatures for duplexes of asODN with RNA-15 and RNA-20 were 63 and 70° C., respectively. For these two RNA targets, the increases in RNase H activity upon photoactivation arose from the greater stability of the DNA hairpin ($\Delta T_m$=17, 10° C.) versus the RNA/asODN duplexes. Free energy calculations gave $\Delta G$ values for asDNA/sDNA, asDNA/RNA-15 and asDNA/RNA-20 at 37° C. in RNase H buffer of -12.4, -14.5, -16.3 kcal/mole, respectively. For the conjugate, $\Delta G$ equal to -17.0 kcal/mole was calculated by determining $\Delta H_d$ and $\Delta S_d$ from the concentration dependence of the melting equilibria using the van't Hoff expression.

Binding RNA-15 or RNA-20 to the DNA hairpin was disfavored thermodynamically, $\Delta G$=2.5 and 0.7 kcal/mole. The decrease in $\Delta\Delta G$ with increasing RNA oligomer length helps to explain the higher background levels of RNA-20 digestion, before photolysis. RNase H has been shown to promote the formation and cleavage of RNA/DNA duplexes, even under conditions where RNA/DNA hybridization is thermodynamically disfavored. After photolysis, the activated asODN/sODN hybrid readily converted to asODN/RNA-15 and asODN/RNA-20 ($\Delta^2 G$=-2.1 and -3.9 kcal/mole). In addition to thermodynamic considerations, the higher background level of RNase H activity for RNA-20 was due to the nature of the blocking group. The 12 complementary bases on the sense ODN were designed to block the binding and degradation of RNA targets with the same 12-base recognition motif. However, the eight mismatched bases of the asODN in the DNA hairpin were able to base pair with RNA-20 and recruit RNase H. Although RNA-20 should be one of the most difficult sequences for this DNA hairpin to photo-discriminate against, the photo-modulation efficiency (1.3±0.2) was slightly over background.

Example 4

Designing Photoactive DNA Hairpins Against a Specific RNA Target

The DNA hairpin exhibited the highest photo-modulation efficiency towards the RNA-15 substrate. Contributing factors were the stability of the DNA hairpin relative to the asODN/RNA-15 duplex (ΔΔG=−2.5 kcal/mole), proper complementarity of the blocking strand (slightly shorter than the target), and the structure of the RNA itself, which limited nonspecific DNA hybridization. The RNA melting temperatures of RNA-15, RNA-20, and RNA-40 were 51° C., 54° C., and 63° C., respectively. The expected correlation between increasing RNA strand length and structure is surprising in view of the higher photo-modulation efficiency for RNA-40 than RNA-20. These targets had the same 20 bases complementary to asODN, and yet RNA-40 exhibited much lower background levels of hydrolysis. Evidently, for targets such as RNA-40, it is important that the asODN has a high degree of complementarity to compete with the stable RNA stem-loop structure. To test this hypothesis, a RNA 40-mer was employed with only 15 complementary bases (CUU GUA CAG AAAUACGGUCCGAAACCA ACC UCU GUU AUU G (SEQ ID NO. 2), underlined bases are identical to RNA-15). No RNase H activity was observed towards this substrate using the photolyzed DNA hairpin, and only 13% digestion was seen with the control asODN.

Notably, in using azobenzene-modified oligos, having a small $\Delta T_m$ of 18° C. necessitated a 10-fold excess of sense ODN relative to asODN, in order to limit RNA/asODN duplex formation. This strategy is not practical for most biological applications since the sense ODN can diffuse away or become degraded inside the cell. Furthermore, introducing an organic chromophore in the middle of an ODN typically lowers the DNA duplex melting temperature by just a few ° C. per blocking group. It was demonstrated that a much larger $\Delta T_m$ can be achieved by conjugating the sense ODN to the asODN via a single photocleavable linker with the PC linker playing a role in stabilizing the conjugate.

Synthesis of S-C5 and S-C6

Synthesis of phosphorothioated DNA conjugates S-C5 and S-C6 was performed as described for C1-C6 in Examples 1-4, with minor modifications. The amine-terminated sense strands and thiol-terminated antisense strands, comprised of DNA phosphorothioate oligonucleotides, were synthesized at the UPenn Nucleic Acid Facility and purified by RP-HPLC with a linear gradient of 5→30% acetonitrile in 0.05 M TEAA in 30 min at 40° C. HPLC traces showed purification of conjugates S-C5 and S-C6.

Example 5

Photocleavable Oligonucletide is Capable of Regulating the Expression of Chordin in Zebrafish An 18-mer asPNA (negatively charged, amine-terminated PNA from Active Motif) targeting the Kozak sequence and start codon of zebrafish chordin mRNA, was attached to a thiol-terminated 12-mer 2'-OMe-RNA sense strand (sRNA) via a 1-(5-(N-maleimidomethyl)-2-nitrophenyl)ethanol N-hydroxysuccinimide ester photocleavable linker (PL). See FIG. 12. The material was synthesized in high yield, after confirming the identity and purity of this compound by MALDI-TOF, HPLC, and gel electrophoresis with P-32 labeled material.

sDNA was found to be toxic in zebrafish embryos, and all embryos injected with either sDNA alone or asPNA-PL-sDNA died within a few hours of injection. Therefore, 2'-OMe sRNA was selected as the blocking strand, and it proved to be nontoxic. It was reasoned that a 12mer sense strand would adequately block the effects of the asPNA, while minimizing the stability of the asPNA-2'-OMe sRNA duplex after photoactivation.

Chordin plays several important roles during zebrafish embryonic development, including dorsal-ventral patterning. UV cleavage of the asPNA-PL-sRNA conjugate yielded the much less stable asPNA/sRNA duplex ($T_m$~70° C.). In this form, it was anticipated that the asPNA would bind complementary chordin mRNA, and thereby block ribosomal protein synthesis.

Figure 17:
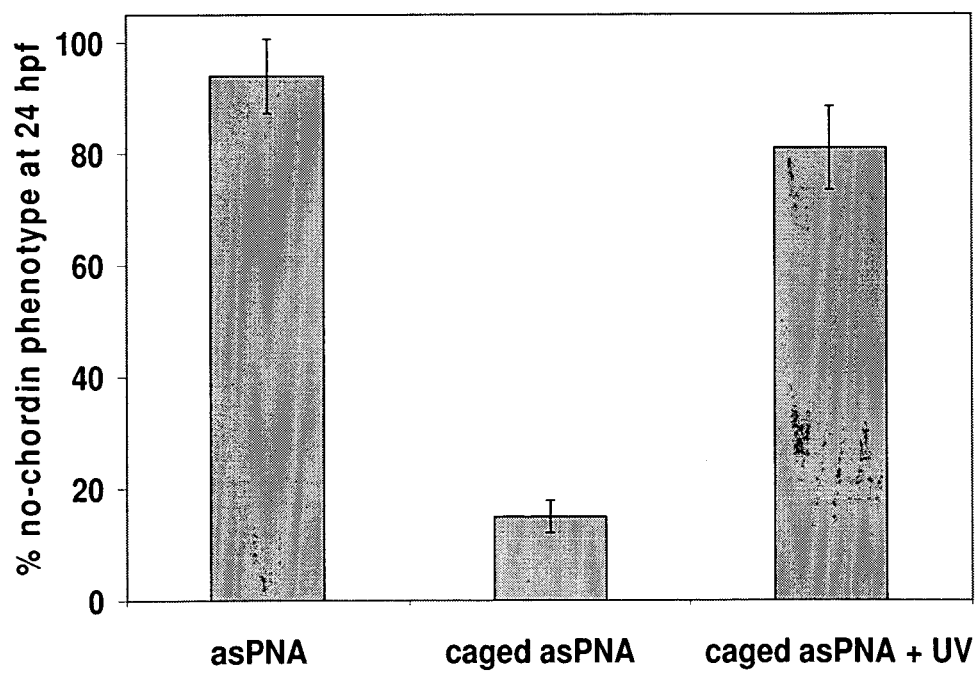
FIG. 17 shows frequency of zebrafish no-chordin phenotype observed at 24 hpf after injection of asPNA or caged asPNA as shown in FIG. 12. Some embryos injected with caged asPNA were UV irradiated at 3 hpf. Error bars show standard deviation from three independent trials.

In order to determine whether low-level UV light had adverse effects on early development, 50 zebrafish (*Danio rerio*) embryos at 3 hours post fertilization (3 hpf) for 0, 5, 10, and 20 min were first irradiated with a UV transilluminator and the phenotypic results were compared at 24 hpf. No differences between zebrafish were observed (FIG. 17A), indicating that the UV light was nontoxic Embryos injected with the amine-terminated asPNA showed obvious morphogenesis at 24 hpf, with a shortened tail characteristic of the 'no-chordin' phenotype (FIG. 17B). Embryos injected with asPNA-PL-sRNA were divided into two dishes. One dish was kept in the dark, the other irradiated. Most embryos that remained in the dark appeared completely normal at 24 hpf (FIG. 17C), indicating that the conjugated sRNA strand blocked binding of asPNA to the target mRNA, and no toxicity from the conjugate was observed. In contrast, most of the irradiated embryos exhibited the no-chordin phenotype at 24 hpf (FIG. 17D). Evidently, UV irradiation activated the asPNA strand, which was subsequently targeted chordin mRNA and inhibited protein expression. A UV confocal microscope may be employed, in order to perturb gene expression on a cell-by-cell basis.

Thus, the thermodynamics of hybridization that were determined using in vitro assays shown in the previous examples seem to be good predictors of activity inside the developing zebrafish embryo. Future experiments can increase the amount of caged asPNA injected into the zebrafish embryos, in order to increase the biological effects while remaining below the toxicity threshold. The modestly higher number of dead embryos observed in the asPNA experiments relative to the uninjected control is likely due to the effects of microinjection itself, and these compounds appear to be nontoxic at biologically relevant concentrations. Irradiation was performed by putting the UV lamp for 8 minutes at a short distance above the embryos.

Example 6

Photocleaved asPNA-PL-sRNA May Remain Hybridized after UV Exposure

Interestingly, embryos containing photoactivated asPNA-PL-sRNA showed a slightly weaker no-chordin phenotype than those injected with asPNA: Compare representative embryos in FIGS. 17B and 17D. Some photocleaved asPNA-PL-sRNA was postulated to have remained hybridized after UV exposure, with an equilibrium between the asPNA/sRNA and asPNA/mRNA duplex forms. This binding competition would lower the effective concentration of asPNA that could bind mRNA and block translation. This hypothesis was tested by comparing the fluorescence intensity of a molecular beacon (5'-FAM-CAG CGATGGAGGGGCTGCTGTGGC GCT G-BHQ1-3' SEQ ID NO. 10) when asPNA, asPNA-PL-sRNA, or photoactivated asPNA-PL-sRNA was added to the molecular beacon solution. Fluorescence from the beacon in the presence of asPNA-PL-sRNA increased roughly 2-fold upon UV irradiation (FIG. 20B). However, when the beacon was mixed with asPNA (in non-duplex form), the observed fluorescence intensity was an additional 4-fold higher. This indicated that only ~25% of the photoactivated asPNA-PL-sRNA hybridized to the molecular beacon.

Figure 18:
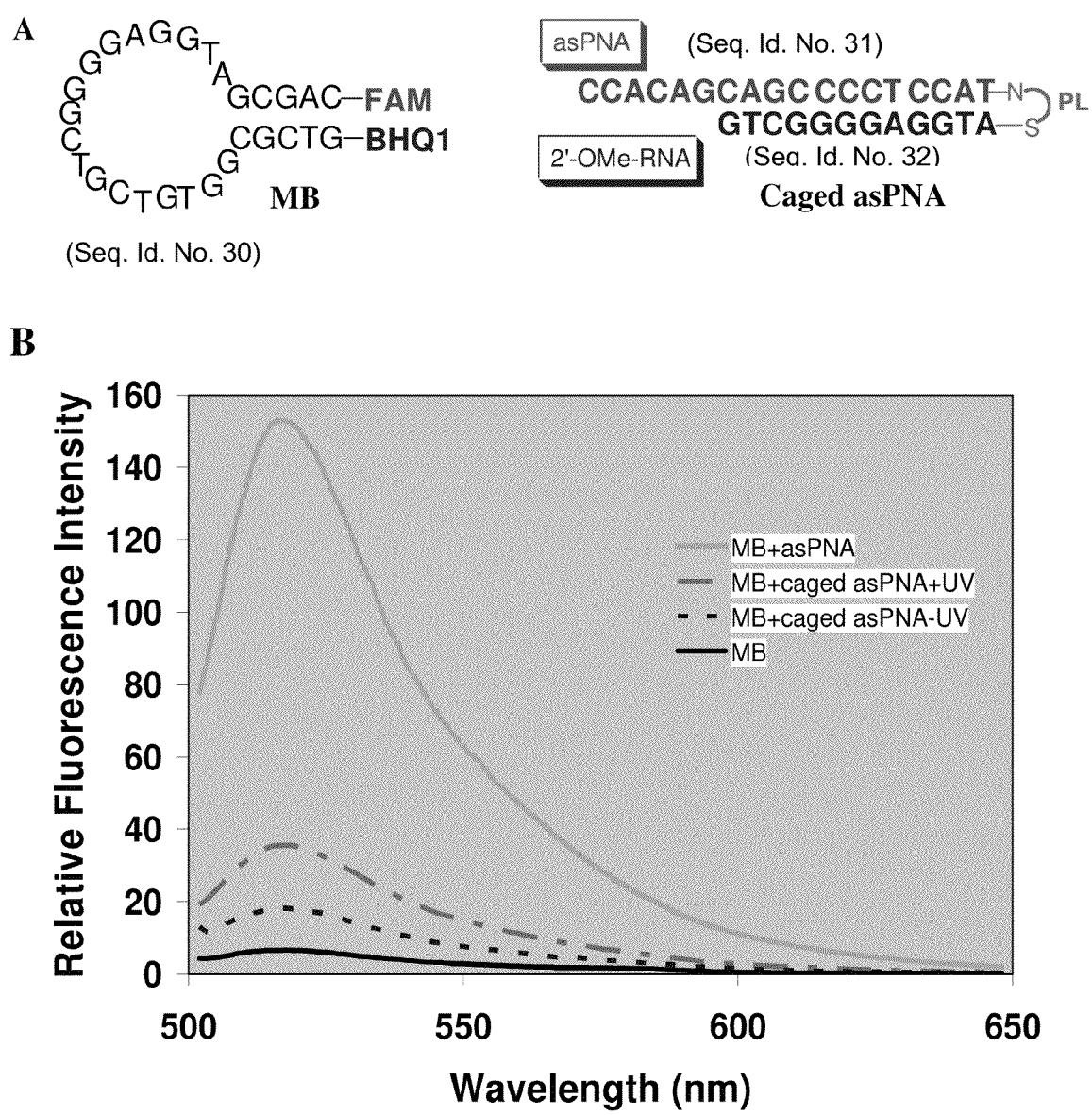
FIG. 18 shows A) Structures of MB and caged asPNA, and B) relative fluorescence intensity of MB, MB+asPNA, MB+caged asPNA, and MB+caged asPNA+8 min photolysis (UV transilluminator, 9 mW/cm$^2$ at 365 nm) at a concentration of 40 nM in 10 mM phosphate buffer at 30° C., $\lambda_{ex}$=488 nm.

FIG. 18 shows that asPNA injection caused 94% of zebrafish embryos to develop the no-chordin phenotype (average of three experiments, n=90). Lower than 100% antisense activity was likely caused by small variations in microinjection efficiency. With injection of caged asPNA, just 15% of embryos (average of three experiments, n=75) developed abnormally, with characteristics similar to 'no-chordin'. This small amount of background activity in the caged samples was due, in part, to exposure to low-level microscope illumination during embryo microinjection (duration ~30 min). Finally, 81% of embryos injected with caged asPNA (average of three experiments, n=75) developed the no-chordin phenotype after photoactivation.

Example 7

Regulating Gene Expression in Zebrafish Embryos Using Light-Activated, Negatively Charged Peptide Nucleic Acids Achieving a molecular understanding of biological processes will require quantitative tools for regulating gene activity with high spatial and temporal resolution. Such methods will allow, for example, real-time functional studies of cellular proteins. One promising approach involves reverse complementary 'antisense' oligonucleotides, such as 'mopholinos' and negatively charged peptide nucleic acids (ncPNAs), which down-regulate target genes in model organisms. Short ncPNAs bind tightly and sequence specifically to complementary mRNA, possess a nuclease-resistant pseudopeptide backbone, and, when targeted to translation initiation sites, block ribosomal protein synthesis. Thus, the application of light-activated 'caging' strategies to ncPNA would provide an "on→off" switch for controlling gene expression (FIG. 14A). It was shown in previous Examples that attaching sterically bulky photolabile groups to oligonucleotides has modest effects on duplex formation. The example describes the synthesis, characterization, and in vivo application of two light-activated ncPNAs whose hybridization to mRNA is conditionally blocked by a complementary 2'-OMe RNA strand (FIG. 14B).

In the present Example and as described in Example 5 above, an amine-terminated, 18-mer antisense ncPNA (Active Motif) targeting the Kozak sequence and start codon of zebrafish chordin mRNA, was attached to a thiol-terminated 12-mer 2'-OMe-RNA sense strand (sRNA) via a 1-(5-(N-maleimidomethyl)-2-nitrophenyl)ethanol N-hydroxysuccinimide ester photocleavable linker (PL). Chordin plays several important roles during zebrafish embryonic development, including dorsal-ventral patterning. UV cleavage of caged PNA-chd ($T_m$>90° C.) yielded the less stable PNA-chd/sRNA duplex ($T_m$=70° C.). In this form, it was anticipated that PNA-chd would bind complementary chordin mRNA, and block protein synthesis.

Figure 19:
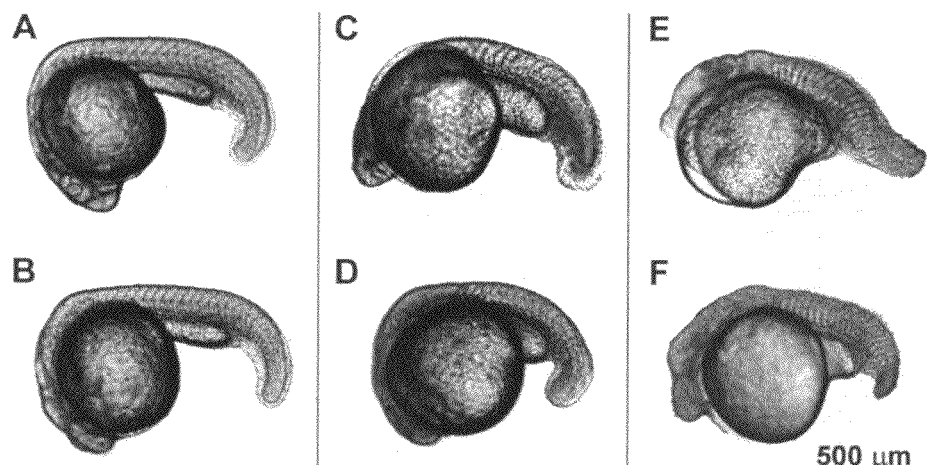
FIG. 19 shows transmitted light images of representative 24-hpf zebrafish embryos. A) Uninjected embryos UV-irradiated at 3 hpf for 8 min developed normally. B) Injection with 0.5 mM caged PNA-chd or caged PNA-boz had no effect in the dark. Embryo shown was injected with caged PNA-chd. C) Embryos microinjected with 0.1 mM PNA-chd exhibited "no-chordin" phenotype. D) Injection with 0.5 mM caged PNA-chd and UV irradiation at 3 hpf gave no-chordin phenotype. E) Embryos microinjected with 0.5 mM PNA-boz exhibited "no-bozozok" phenotype. F) Injection with 0.5 mM caged PNA-boz and 8-min UV-irradiation at 2 hpf gave no-bozozok phenotype.

Control experiments showed no differences between UV irradiated and non-irradiated zebrafish embryos (FIG. 19A). 95% of embryos injected with native PNA-chd showed a shortened tail and reduced brain characteristic of the chordino (no chordin) phenotype at 24 hpf (average of three experiments, n=90; FIG. 19C). Lower than 100% antisense activity was due to small variations in microinjection volume. Embryos injected with caged PNA-chd (average of three experiments, n=150) were divided, with one dish kept in the dark, the other irradiated for 8 min. 85% of embryos that remained in the dark appeared completely normal at 24 hpf (FIG. 19B), indicating that the conjugated sRNA strand blocked binding of PNA-chd to target mRNA. The other 15% of embryos showed a mild chordino phenotype at 24 hpf This was likely caused by features of the caged PNA-chd, such as rRNA quadruplex structure, which reduced the blocking effects. Trace amounts of PNA-chd may also have contributed to this result. Photoactivation of caged PNA-chd produced the chordino phenotype in 81% of embryos (FIG. 19D). As expected when chordin is down-regulated, these embryos also showed greatly reduced expression of the gene otx2. The high thermal stability of the PNA-chd/sRNA duplex contributed to the lack of a chordino phenotype in 19% of the irradiated embryos. Photocleavage occurring within 8 min in buffer and zebrafish was confirmed by gel electrophoresis using fluorescently labeled PNA conjugates.

Phenotypic differences were investigated between embryos containing uncaged PNA-chd or native PNA-chd. Photoactivation of caged PNA-chd gave an equilibrium between PNA-chd/sRNA (inactive) and PNA-chd/mRNA (active) duplex forms, which was assayed in a molecular beacon experiment. These results were validated with zebrafish dose-response experiments which showed that phenotypes were equalized by injecting 5-fold less native PNA-chd (0.1 mM, FIG. 2C) than caged PNA-chd (0.5 mM solution), followed by UV irradiation (FIG. 19D). Caged PNA-chd blacked chordin expression in a light- and concentration-dependent manner.

Example 8

Photocleavable Oligonucletide is Capable of Regulating the Expression of Bozozok in Zebrafish To test the specificity of caged ncPNA, a second gene was targeted, bozozok, with important roles in organizer formation during early zebrafish development. An 18-mer ncPNA was previously identified for bozozok that produced definitive gene knockdown. This PNA-boz sequence was attached via PL to an 8-mer sense 2'-OMe-RNA (FIG. 12B). The shorter blocking strand was employed to promote efficient PNA-boz/mRNA duplex formation after in vivo photoactivation. Melting temperature experiments indicated that caged PNA-boz, $T_m$=80° C., was much more stable than uncaged PNA-boz, $T_m$=39° C. The large $\Delta T_m$ of −41° C. validated the caged ncPNA strategy, and facilitated removal of unreacted ncPNA/sRNA from caged PNA-boz by HPLC.

Embryos injected with caged PNA-boz and left in the dark developed normally, whereas embryos injected with native PNA-boz (FIG. 19E) or injected with caged PNA-boz then irradiated for 8 min at 2 hpf showed the typical bozozok null ("no-bozozok") phenotype at 24 hpf with block-shaped somites, neurectodermal defects, and absence of axial mesodermal tissues (FIG. 19F). Some embryos were fixed at 5-6 hpf at the early gastrula stage and visualized by in situ hybridization to detect the expression of goosecoid (gsc), which is a marker of the dorsal organizer known to be dependent on bozozok. Whereas uninjected embryos showed gsc expression in the dorsal organizer (FIG. 20A), PNA-boz injection caused complete loss of gsc in 90% of embryos (FIG. 20B), as expected for loss of bozozok function. Of embryos injected with caged PNA-boz, 95% showed no effect on gsc expression at 6 hpf (FIG. 20C). In contrast, irradiation at 2 hpf greatly reduced gsc in 85% of embryos (FIG. 20D). These data highlight the power of caged ncPNAs to control complex gene networks.

In summary, Examples 7 and 8 show the efficiency of the caged oligos in regulating two developmentally important genes in zebrafish embryos using caged negatively charged PNAs. UV light efficiently restored antisense activity.

Example 9

Figure 11:
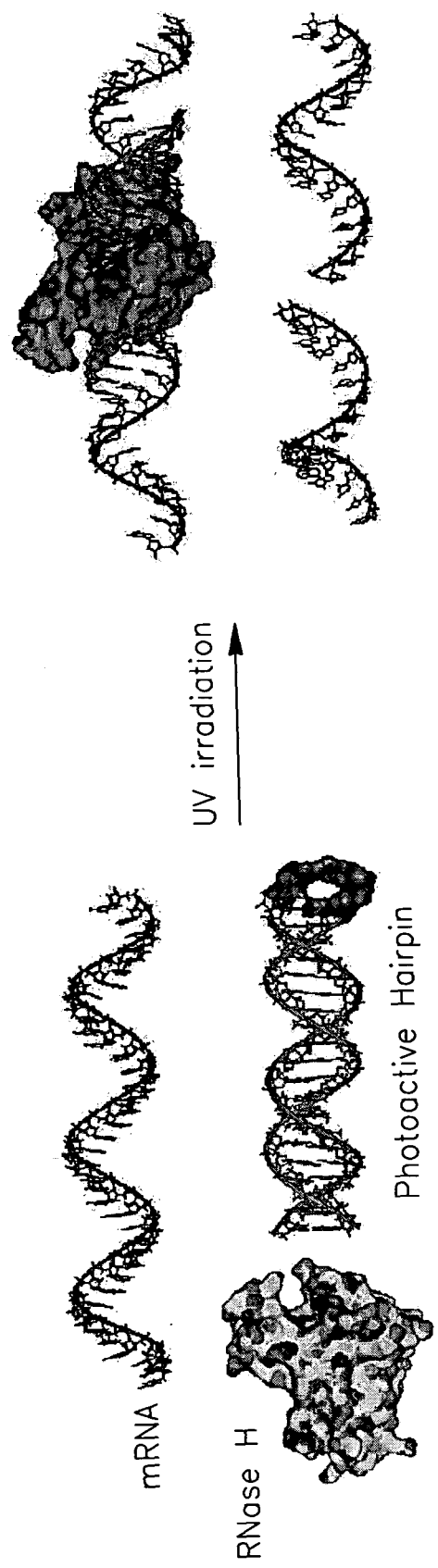
FIG. 11 shows photoactive asODN hairpin strategy. Photocleavage reveals the asODN which binds to target c-myb mRNA. RNase H degrades c-myb in the asODN-mRNA duplex. DNA works for these in vitro assays. Phosphorothioated analogs are proposed for studies in leukemia cells and neurons.

Regulating Gene Expression in Human Leukemia Cells Using Light-Activated Oligodeoxynucleotides In previous examples, the stability of DNA hairpins relative to the corresponding DNA/RNA hybrids was shown to influence the extent of RNA degradation by RNase H. Based on this observation, several light-activated asODN-PL-sODN conjugates were designed to investigate factors important in controlling this enzymatic process (FIG. 11), both in biochemical and cellular assays.

In this Example a cancer-related gene was down-regulated using light-activated oligonucleotides. Caged oligos were targeted against the proto-oncogene c-myb in human K562 (leukemia) cells. c-MYB is a transcription factor that regulates cellular differentiation and proliferation and is regulated by complex mechanisms that control its repressed oncogenic activity. Control of such critical functions also suggests a potential role for MYB in leukemic transformation. MYB has been shown to represent a legitimate therapeutic target in patients with hematologic malignancies, because normal cells are more tolerant of transient MYB deprivation. Reverse complementary ODNs that target a 20-base region within c-myb mRNA, 326←345, have been shown to degrade c-myb by recruiting RNase H.

Figure 12:
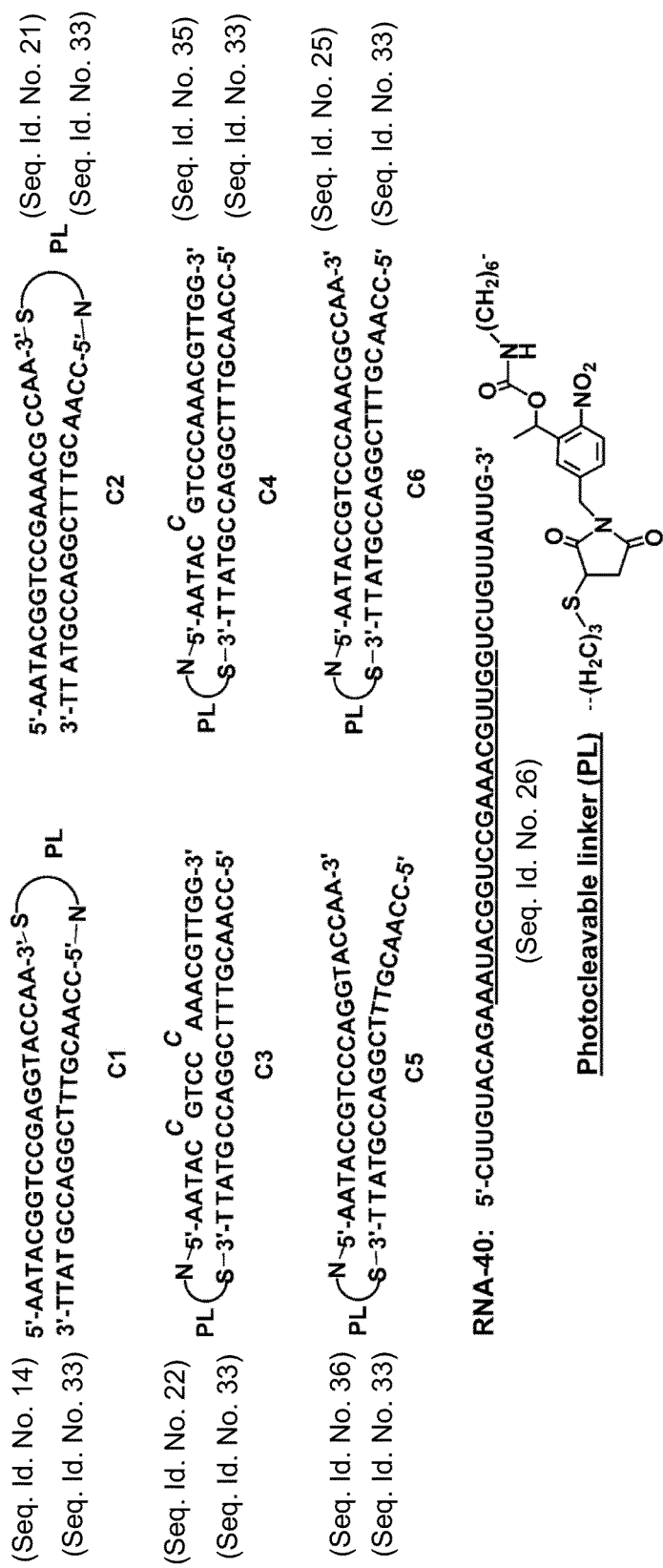
FIG. 12 shows sequences of six photoactive DNA hairpins representing asODN-PL-sODN conjugates, C1-C6, and targets, RNA-20 and RNA-40; structure of the photocleavable linker, PL. Underlined bases in RNA-40 are identical to RNA-20, correspond to bases 326-345 of c-myb.

A series of six photoactive DNA conjugates (C1-C6, FIG. 12) was synthesized by covalently attaching a 20-mer asODN targeting c-myb residues 326←345 to a complementary sense strand via a 1-(5-(N-maleimidomethyl)-2-nitro-phenyl)ethanol N-hydroxysuccinimide ester. This heterobifunctional photocleavable linker (PL) was designed to react with thiol and amine functionalities on opposite ends (FIG. 12). The size and directionality of the hairpin loop was varied, and the number and placement of complementary bases in the stem, in order to stabilize the "caged" asODN-PL-sODN conjugates relative to the corresponding asODN/sODN duplexes. The increase in RNase H activity as photomodulation efficiency was defined as: [RNA digested after photoactivation]/[RNA digested before photoactivation]. C5 and C6 showed the greatest photomodulation efficiency in biochemical RNase H assays, and were subsequently synthesized with a more nuclease-resistant phosphorothioate backbone. These conjugates, S-C5 and S-C6, were tested in K562 cells for their ability to photoregulate the digestion of c-myb mRNA by RNase H, as well as c-MYB protein knockdown. These studies point the way towards new cellular gene regulation strategies and photodynamic therapies.

Design and Optimization of Photoactive Hairpins

Previous Examples with C5 identified two routes for improving the photomodulation efficiency: 1) make the conjugate more kinetically or thermodynamically resistant to binding to the target mRNA, thereby lowering the RNase H background activity; 2) destabilize the photoactivated asODN/sODN duplex, thereby promoting asODN/mRNA hybridization, and increasing the percentage of RNA-40 degradation by RNase H.

In order to lower background RNase H activity, we sought to modify the eight unpaired bases in the stem of C5. The accessibility of these bases could have the undesired effect of allowing hybridization of asODN-PL-sODN to RNA-40. C1 and C2 were designed to re-orient the loop and hybridize the ends of the hairpin stem, which we reasoned would lower background RNase H activity. C1 had the same 12 complementary bases as C5, but moving the photocleavable linker increased the size of the loop by 16 nucleotides. C2 had four additional complementary bases, which created a loop with 8 nucleotides. Photoactive oligos C3 and C4 were designed with 2 and 1 mismatches in the sense strand, respectively. The mismatches were chosen based on calculations on the HyTher™ server, which helped to identify sites that would particularly destabilize the asODN/sODN duplex. In this way, it was expected to increase the thermal stability of C3 and C4 relative to their photoactivated duplexes, thereby increasing $\Delta T_{m(conjugate-duplex)}$. In addition, C4 was expected to be particularly stable and show low RNase H background activity, based on its 19 base pairs. The significant complementarity in C3 and C4 between the antisense and sense strands eliminated overhangs that might hybridize with RNA-40. Finally, C6 was designed to be more stable than C5, with the addition of four complementary base pairs in the stem. We note that C6 is a cognate of C2, with the same 16 complementary bases, but in the reverse orientation relative to the loop. Compared to C5, the conjugate C6 had only four non-complementary bases and was expected to associate less strongly with RNA-40, and therefore decrease the background RNase H activity.

To test the thermal stability of these conjugates relative to the corresponding asODN/sODN duplexes, UV absorbance melting transitions were measured in standard RNase H buffer. As shown in Table 1, with an increase in the loop from 8 bases (C2) to 16 bases (C1), the melting temperature ($T_m$) of the conjugate decreased 7° C. Two base mismatches destabilized C3 by 10° C. relative to C4, with only one mismatch. Interestingly, C6 had the highest melting temperature ($T_m$=84° C.), which was 3° C. higher than C2 with identical matching base pairs. This provides additional evidence that a small loop formed by the PL in joining asODN and sODN strands is most effective at stabilizing the conjugate. Upon irradiation, all duplexes became less stable, with melting temperatures lowered by 17-29° C.

TABLE 1

Mass characterization, melting temperatures, and photomodulation efficiencies for conjugates C1-C6, showing decrease in thermal stability and increase in RNase H activity upon photoirradiation

| Photoactive Conjugate | Mass (calc) | Mass (expt) | $T_m^a$ (° C.) | $T_m^a$ (° C.) (cleaved) | $\Delta T_m$ (° C.) | Photomodulation Efficiency[b] |
|---|---|---|---|---|---|---|
| C1 | 12838.2 | 12862.5 | 74 | 51 | −23 | 1.5 |
| C2 | 12807.1 | 12803.4 | 81 | 63 | −18 | 3.5 |
| C3 | 12829.4 | 12858.6 | 68 | 47 | −21 | 1.2 |
| C4 | 12789.4 | 12770.0 | 79 | 62 | −17 | 3.4 |
| C5 | 12838.4 | 12838.1 | 80 | 51 | −29 | 4.4 |
| C6 | 12807.4 | 12819.2 | 84 | 63 | −21 | 6.0 |

[a]Melting temperatures were determined from the peak of the first derivative plot of $Abs_{260}$ vs. temperature in standard RNase H buffer.
[b]Photomodulation efficiency is the n-fold increase in RNA-40 cleavage elicited by photoactivation, observed in a 1-h RNase H assay with 1 unit enzyme.

Figure 20:
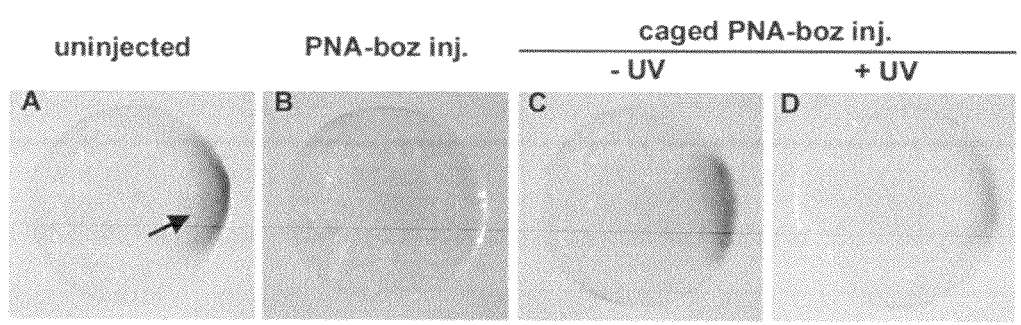
FIG. 20 shows the effect of PNA-boz on goosecoid mRNA levels in the dorsal organizer at 6 hpf. A) Uninjected wild-type embryos showed gsc (black stain) in the organizer (identified with arrow). B) Injection of PNA-boz resulted in loss of gsc. C) Injection of caged PNA-boz did not affect gsc expression. D) UV activation of caged PNA-boz at 2 hpf caused reduction of gsc mRNA levels.
Figure 21:
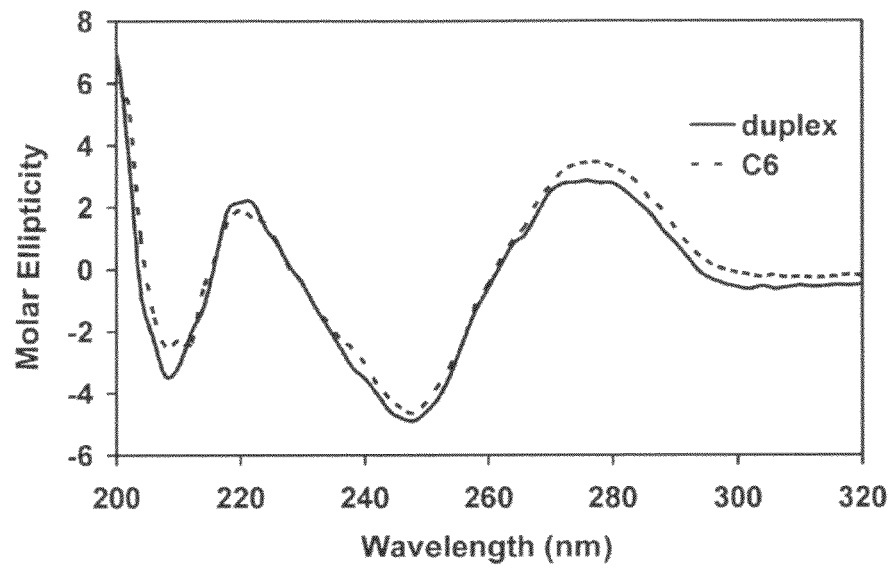
FIG. 21 shows molar ellipticity ($[\theta]\times10^{-5}$·deg·cm$^2$·dmol$^{-1}$) of C6 and its corresponding duplex (30 μM in 1× RNase H buffer) measured by CD spectroscopy.

Circular dichroism (CD) spectroscopy provided a convenient method for assessing the conformational structure of the oligonucleotides. FIG. 20 shows the CD signal for C6, which was representative of the conjugates. The conjugates' optical signature agreed very well with the oligonucleotide duplexes of the same sequence. This indicated that the photocleavable linker had little effect on the fully base-paired helical structure.

Photomodulation of RNA Digestion by RNase H with Photoactive Conjugates

Figure 22:
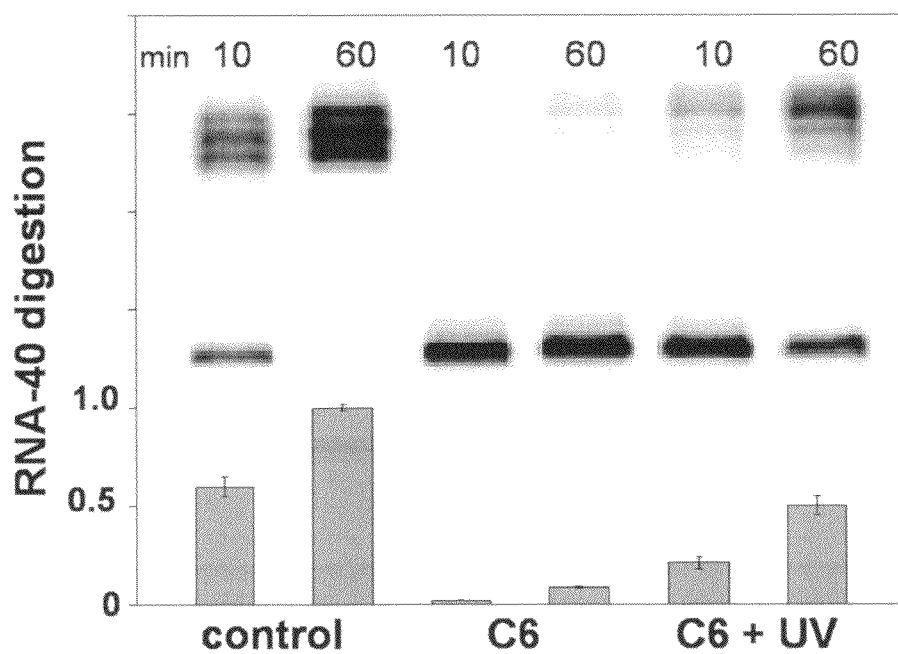
FIG. 22 shows denaturing PAGE (20%) analysis of RNA-40 digestion with 2 μM [γ-$^{32}$P]-labeled RNA-40, 0.01 μM photo-activated C6 and 1 unit RNase H in RNase H buffer at 37° C. Lanes 1-2, control asODN at 10 and 60 min; Lanes 3-4, C6, at 10 and 60 min; Lanes 5-6, C6, at 10 and 60 min that had been activated with UV light (355 nm, 36 mW/cm$^2$) for 10 min. Each blue bar is the average of three separate trials.

RNase H activity was studied with RNA oligonucleotide, RNA-40 (40-mer), as shown in FIG. 12. Digestion of the RNA target was compared between solutions containing the control single-stranded asODN (CCAACGTTTCGGACCG-TATT (SEQ ID No. 11)) or a photoactive asODN-PL-sODN conjugate. FIG. 22 shows the typical gel from an RNase H assay experiment with 2 µM [γ-$^{32}$P]-labeled RNA-40, 0.01 µM irradiated C6, and 1 unit RNase H in standard RNase H buffer at 37° C. The first two lanes are the cleavage pattern with control single-stranded asODN at 10 and 60 min, followed by C6 at 10 and 60 min. The last two lanes show the cleavage pattern with C6 at 10 and 60 min after irradiation. The bar graph below the gel in FIG. 22 shows the relative amount of RNA digestion observed under each condition, where a value of 1 equals complete digestion. Using C6 in a 1-h experiment, 50% of the total RNA-40 target was digested after irradiation, as compared to a background level of 8.6% without irradiation and ~100% RNA degradation for the control single-stranded asODN. This corresponded to a roughly 6-fold increase using 1 unit of enzyme, 1 h after photoactivation. Photomodulation efficiency was even higher early in the reaction, with 10-fold higher RNase H activity (2%→21%) observed at 10 min. The UV light used in these experiments had no effect on the enzyme or RNA stability. Control experiments confirmed that RNase H hydrolyzed RNA-40 only when hybridized with asODN.

Figure 23:
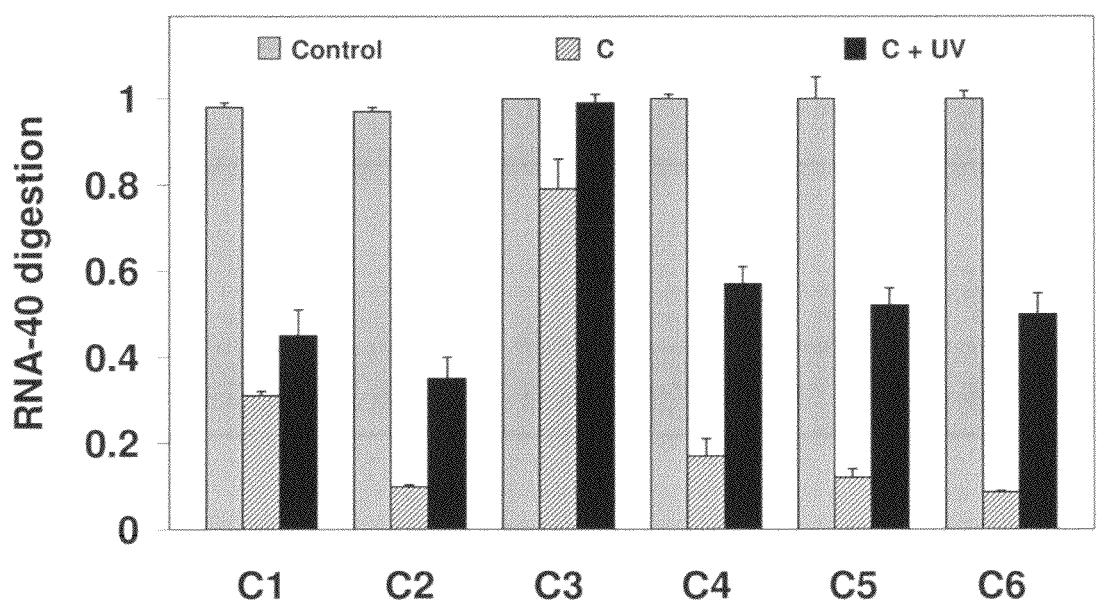
FIG. 23 shows RNase H assay showing the digestion of RNA-40 (2 μM) in 60 min at 37° C. with C1-C6 (0.01 μM) and 1 unit RNase H. Each control column shows the hydrolysis of RNA-40 with control asODN. UV light (355 nm, 36 mW/cm$^2$) was used to irradiate the samples. Error bars signify standard deviation from 3 separate trials.

The ability of each conjugate to photomodulate RNA-40 digestion was tested under the conditions of 2 mM [γ-$^{32}$P]-labeled RNA-40, 0.01 mM conjugate, and 1 unit RNase H at 37° C. As shown in FIG. 23, loop size had a large effect on RNA-40 digestion by RNase H before irradiation: 31% for C1 compared to 9.8% for C2, indicating roughly 3-fold less digestion with the smaller loop. And upon irradiation, the photomodulation efficiency in a 1-h experiment was 1.5 for C1 and 3.5 for C2 with high background level for C1 before irradiation. This difference is presumed to be due to the difference in thermal stability between these two conjugates: $\Delta T_{m\ C2-C1}=7°$ C. For C3, just 1.2-fold photomodulation was observed, with much higher background of 80% for C3 before irradiation. This result is explained by the C3 melting temperature, $T_m=68°$ C., while the $T_m$ for the target duplex (asODN/RNA-40) was 71° C. Thus, the equilibrium disfavored the conjugate relative to the asODN/RNA-40 duplex. With only one mismatch in C4, the thermal stability ($T_m=79°$ C.) was greatly improved. When compared to the even more thermally stable conjugates C2, C5, and C6, greater enzyme background activity was observed for C4, which led to a lower photomodulation efficiency of 3.4. In these biochemical assays, background activity was strongly correlated with conjugate melting temperature. Among the six photoactive conjugates, the most thermally stable was C6, $T_m=84°$ C. (see Table 1). Largely based on this stability, C6 gave the best photomodulation efficiency, with a 6-fold increase in RNA digestion in the 1-h enzymatic assay. Results with C6 clearly demonstrated that stabilizing the conjugate gave lower levels of background RNA digestion by RNase H.

RNase H Concentration Dependence on RNA Digestion Photomodulation Efficiency

Figure 24:
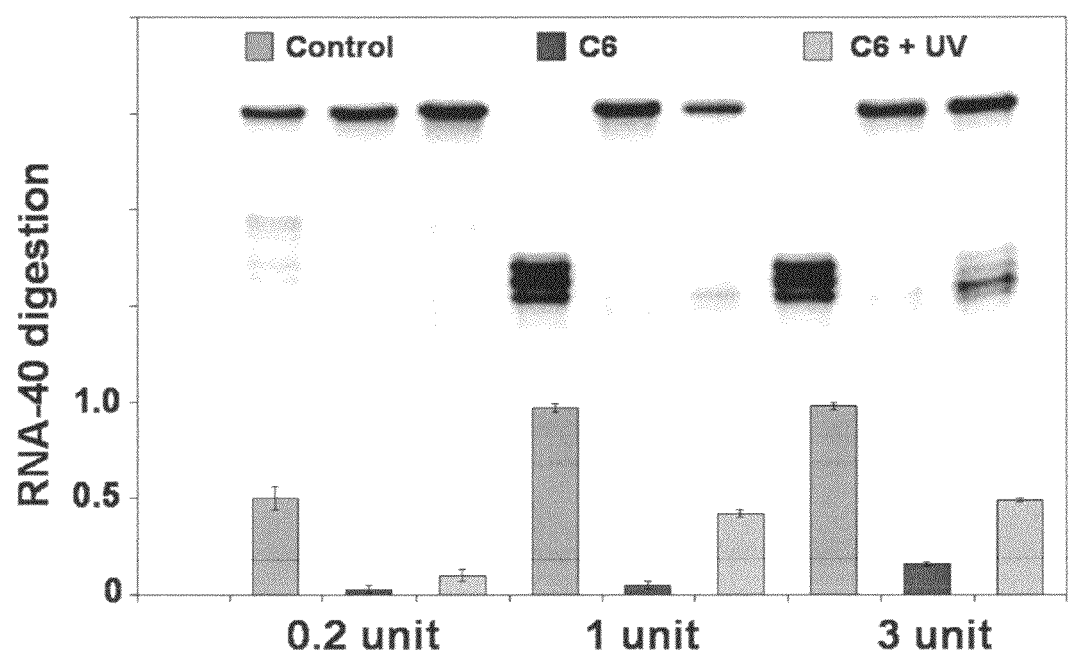
FIG. 24 shows denaturing PAGE (20%) analysis of RNA-40 digestion in 30 min by 0.2, 1, or 3 units of RNase H with 2 μM [γ-$^{32}$P]-labeled RNA-40, 0.01 μM C6 in RNase H buffer at 37° C. Lanes 1-3, control asODN, C6 and cleaved C6 with 0.2 unit RNase H; Lanes 4-6, control asODN, C6 and cleaved C6 with 1 unit RNase H; Lanes 7-9, control asODN, C6 and cleaved C6 with 3 units RNase H, C6 was photocleaved with UV light (355 nm, 36 mW/cm$^2$) for 10 min. The columns show the ratio of degraded RNA to total RNA, data from 2 or 3 independent trials.

The effect of the amount of RNase H in solution on RNA degradation was also tested using C6 (2 µM [γ-$^{32}$P]-labeled RNA-40, 0.01 µM C6 at 37° C.). The gel trace in FIG. 24 showed the pattern of RNA-40 digestion using photoactive conjugate C6 with different amounts of RNase H in a 30-min assay at 37° C. The amount of enzyme had little effect on the control reaction, but had a great influence on the reactions with C6. The gels were quantified using ImageQuant, with the results of RNA digestion shown in the bar graph for each lane (FIG. 24). In 30 min, virtually all RNA-40 in the control experiment with the single-stranded asODN was digested using 1 unit and 3 units RNase H, while for the conjugate C6, there was roughly 3-fold more RNA-40 digestion using 3 units of enzyme (16%) than 1 unit of enzyme (5%). After irradiation of C6, relative amounts of RNA-40 digestion were similar, 42% with 1 unit RNase H and 49% for 3 units RNase H. The thermal stability data cannot predict exactly the differences in RNA digestion, where only the amount of enzyme is varied. However, these studies are relevant to biological experiments, as the amount of RNase H can vary considerably between different cell types, tissues, and species.

RNA cleavage by RNase H is a three-component system requiring the presence of target RNA, the asODN, and RNase H. However, experiments have shown that the process of RNA degradation is more complicated than simple stepwise formation of asODN/RNA duplex, followed by RNase H cleavage. Detailed thermodynamic measurements and gel mobility shift assays showed no hybrid duplex formation with some structured asODNs, especially with hairpin structures, while target RNA could still be cleaved by RNase H. This indicated that RNase H promotes the formation and cleavage of DNA/RNA duplexes, even under conditions where RNA/DNA hybridization is thermodynamically disfavored. These previous studies help to explain why RNase H activity persisted in the biochemical assays even for conjugates with melting temperatures over 80° C.

Effect of Initial RNA/DNA Ratio on Photomodulation Efficiency

Different initial ratios of RNA/DNA were studied for photomodulation of RNA-40 digestion with a fixed concentration of C6 (0.01 µM) and 1 unit RNase H in RNAse H buffer at 37° C. When the ratio of RNA-40/C6 was 200, 50, and 10, RNA-40 cleavage was 8.6%, 12%, and 13% in 1-h experiments. With irradiated samples, the cleavage was 50%, 36%, and 39% with an increase of about 6-fold, 3-fold, and 3-fold, respectively. DNA conjugate C2 gave similar results, with a 3.5-fold and 2.9-fold increase in RNA-40 digestion after irradiation, with RNA-40/C2 ratios of 200 and 10, respectively. Under the same conditions, in this range of enzyme concentrations, RNA-40 was completely degraded by RNase H in the presence of the control asODN. These data indicated higher photomodulation efficiencies at the largest RNA/DNA ratios. Thus, light-activated oligodeoxynucleotides are the most effective in cells where both the concentration of RNase H and the effective (accessible) concentration of target RNA are high.

Cell Studies

To determine the effects of the photoactivatable conjugates in living cells, conjugates S-C5 and S-C6 were both targeted to the c-myb proto-oncogene mRNA (GenBank accession number: M15024) by nucleofection into K562 cells (see Materials and Methods). K562 cell viability was determined post nucleofection and after 5 or 10 min UV light exposure. UV irradiation itself did not appear to be toxic. However, nucleofection of conjugates followed by a 10 min UV exposure was not tolerated by the cells (>75% cell death calculated using Trypan Blue exclusion). Therefore, a less harsh treatment regimen was developed. Cells were allowed to recover in the incubator for 3 h after nucleofection, after which the cells were UV irradiated for 5 min. This strategy appeared well tolerated (<50% cell death) and was subsequently adopted for the experiments reported below.

Figure 25:
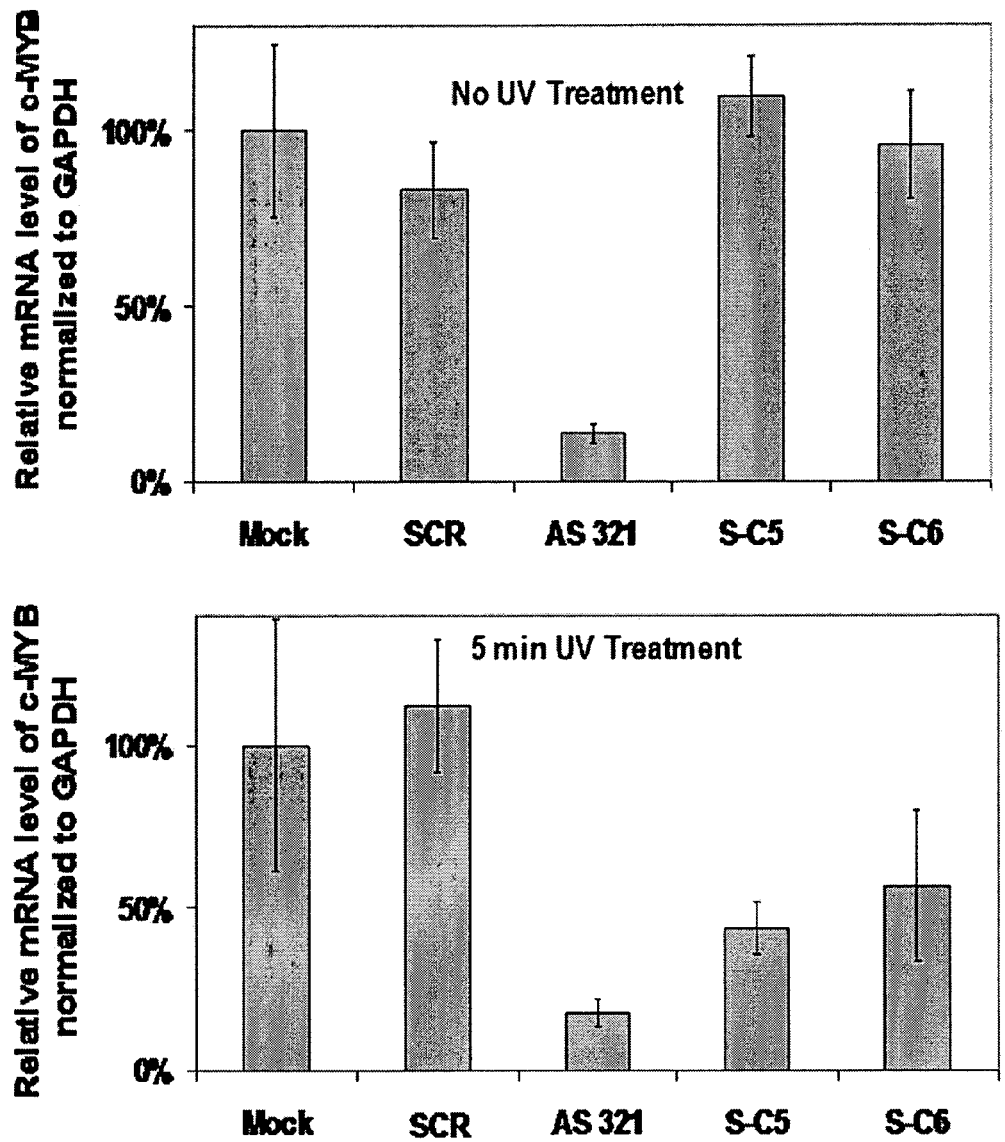
FIG. 25 shows quantitative real-time PCR (QRT-PCR) assay performed on RNA isolated from nucleofected KS62 cells. Data presented are a ratio of the number of copies of c-myb mRNA relative to GAPDH mRNA, which corrects for variations in cell number and viability, and indicates c-myb-specific targeting. Mock cells were nucleofected with buffer in the absence of DNA, and other data were normalized to the Mock data, for which the ratio of gel intensities (c-myb/GAPDH) was set to 100%. mRNA analysis was done 24 h post-nucleofection. Error bars show standard deviation from the average of data from at least three independent trials.

FIG. 25 shows that among the two controls and three experiments, only AS 321, the 20-mer fully phosphorothioated asODN, 5'-CCAACGTTTCGGACCGTATT (SEQ ID No. 12), targeting the same c-myb 326←345 sequence, was effective in decreasing mRNA levels. Relative to the Mock (buffer-nucleofected) control, 86% of c-myb mRNA target was eliminated 24 h after nucleofection with AS 321. Fully phosphorothioated, scrambled ODN (SCR, GAATGTGACATTTCGACACG (SEQ ID No. 13)) showed no biological activity, which confirmed sequence specificity in the interaction with target c-myb mRNA. Pre-irradiation, S-C5 and S-C6 showed the same level of c-myb mRNA as the Mock control, which indicated no discernible background activity for these caged constructs. As a separate control, in the Mock nucleofected cells that were UV-irradiated for 5 min, no statistically significant differences in c-myb mRNA levels were observed. This indicated that the UV light alone was not responsible for down-regulating c-myb. And, cells nucleofected with AS 321 showed identical mRNA "knockdown", pre- and post-UV irradiation, which indicated that there were no particular synergistic effects between the antisense molecule and UV light.

However, c-myb mRNA levels were substantially reduced in cells that had been nucleofected with S-C5 (56% knockdown) or S-C6 (43% knockdown), and subsequently UV-irradiated for 5 min. It was expected that the level of knockdown would be less for the photoactivated conjugates than AS 321, as the sODN remained within the cell and presumably competed with target mRNA for hybridization to the asODN. In zebrafish embryos, it was found that 5-fold more caged ncPNA than native ncPNA was required to achieve similar gene knockdown after photoactivation.

Figure 6:
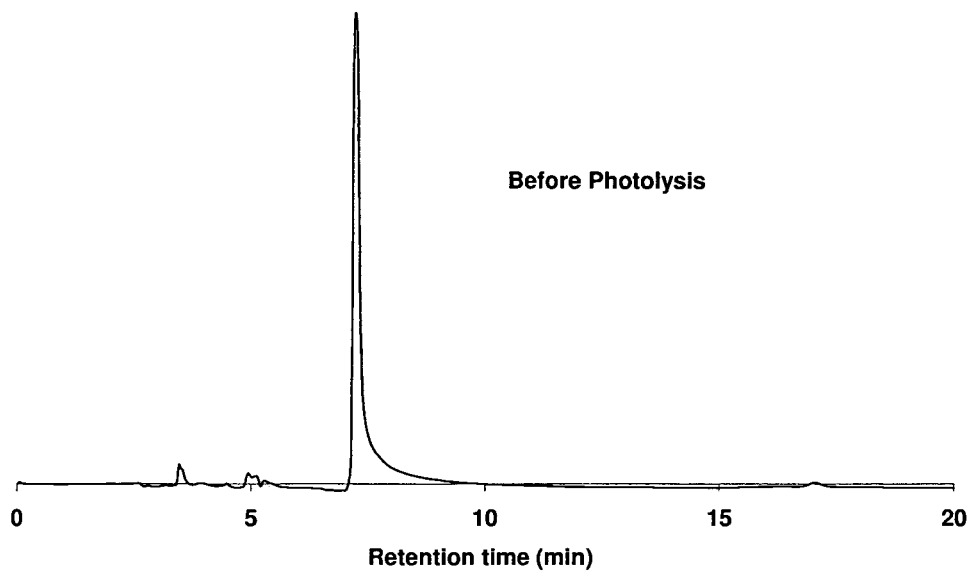
FIG. 6 shows a trace of conjugate, before and after photolysis with 355 nm light.
Figure 6:
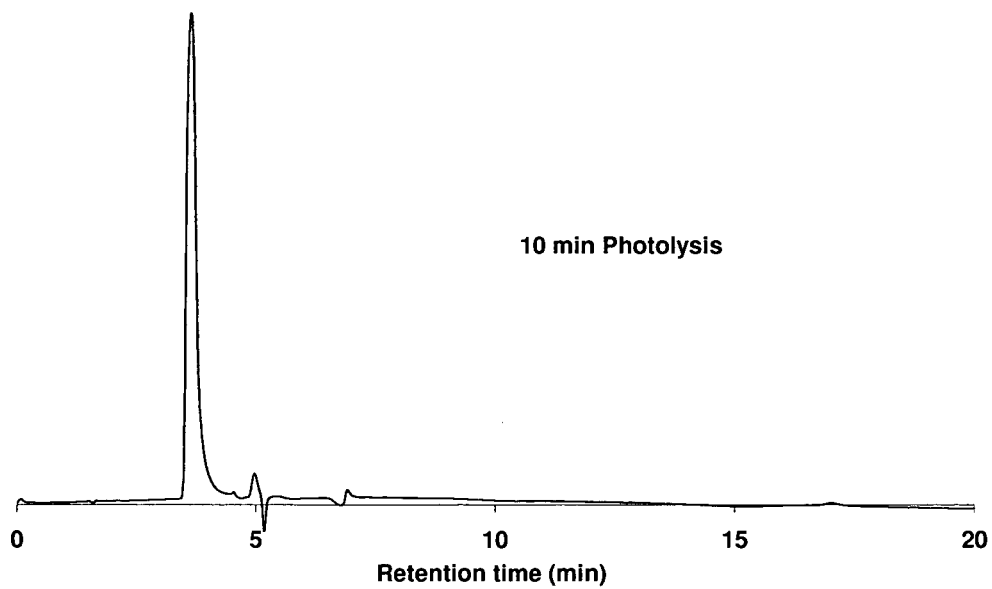
Figure 7:
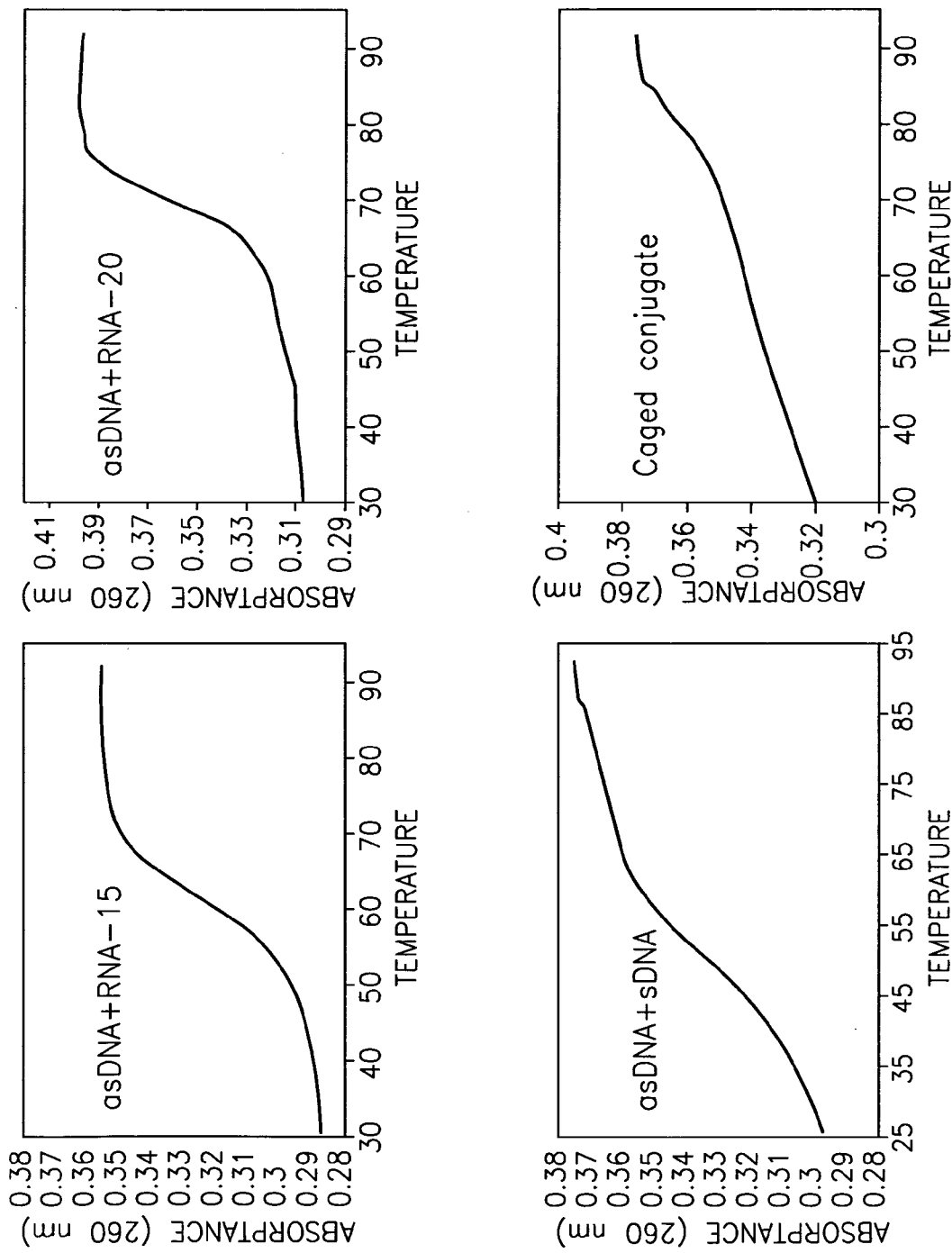
FIG. 7 shows melting curves for asDNA with RNA-15, RNA-20, or sDNA and the conjugate.
Figure 8:
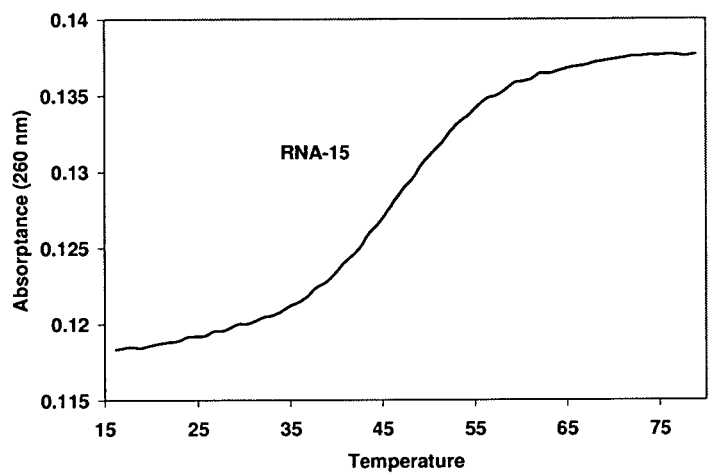
FIG. 8 shows melting curves for RNA-15 (A), RNA-20 (B), and RNA-40 (C).
Figure 8:
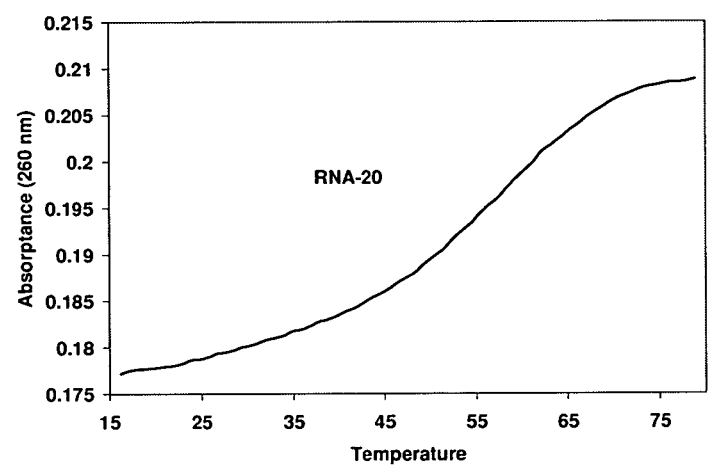
Figure 8:
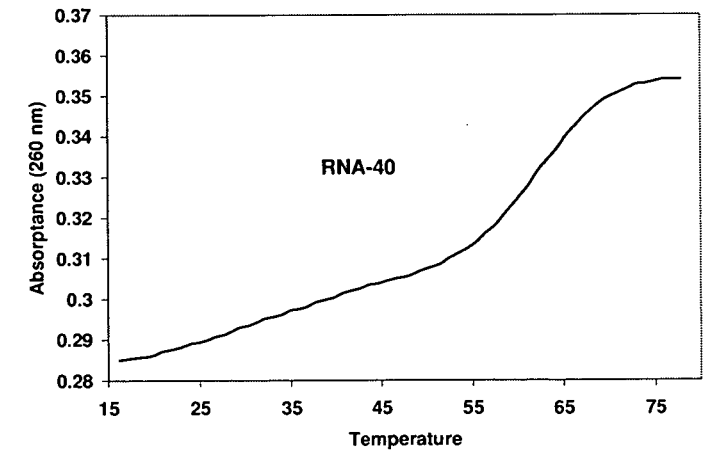
Figure 9:
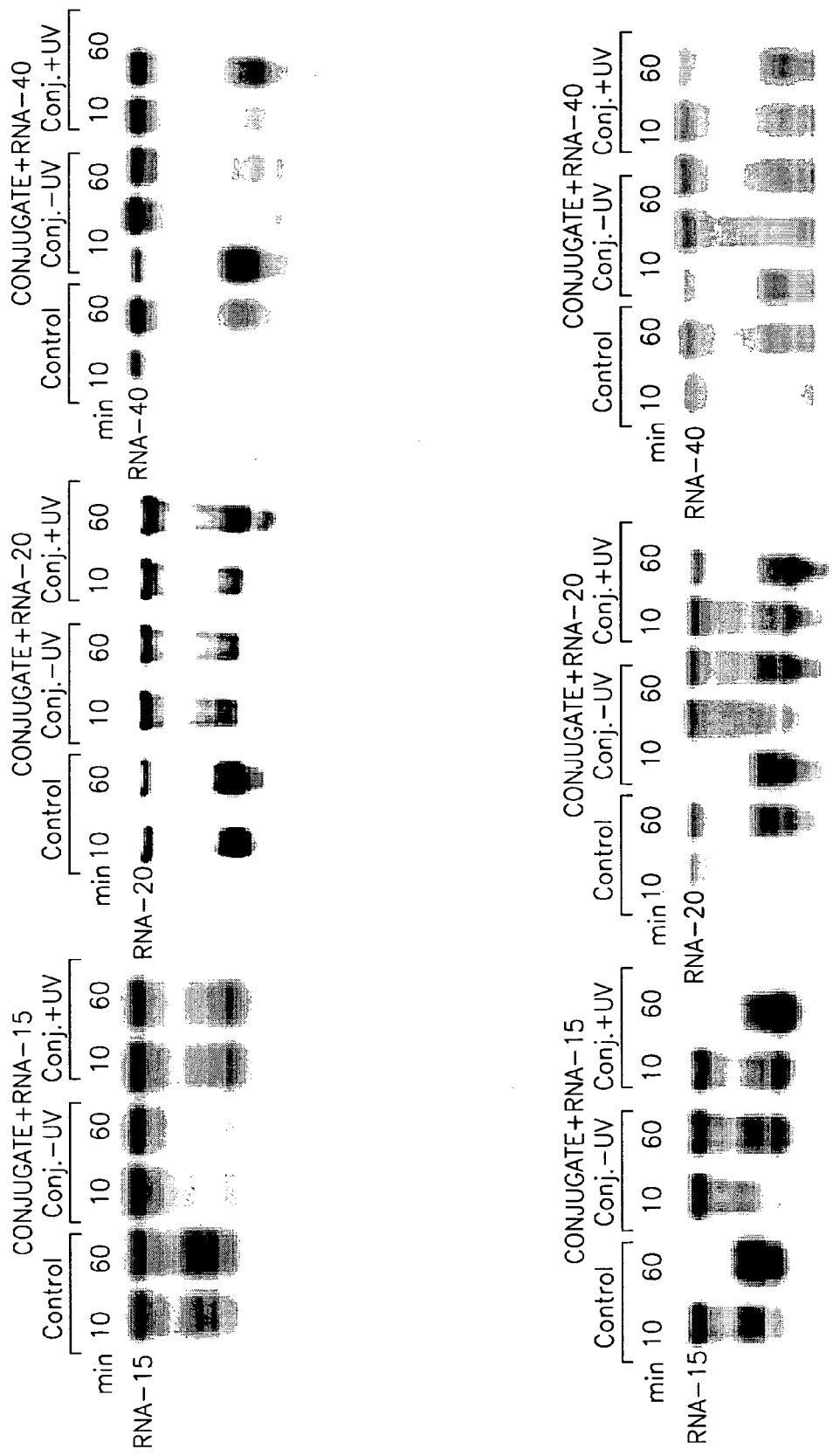
FIG. 9 shows the denaturing polyacrylamide gel electrophoresesis (PAGE, 20% for RNA-15 and RNA-20, 15% for RNA-40) analysis of RNase H assay with RNA-15, RNA-20, and RNA-40.
Figure 10:
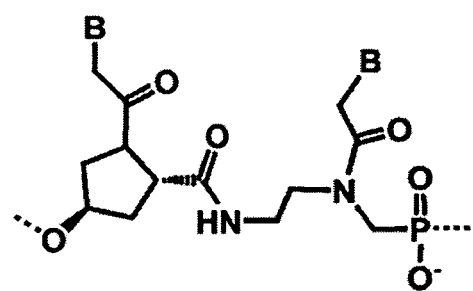
FIG. 10 shows the structure of negatively charged peptide nucleic acid (ncPNA).
Figure 26:
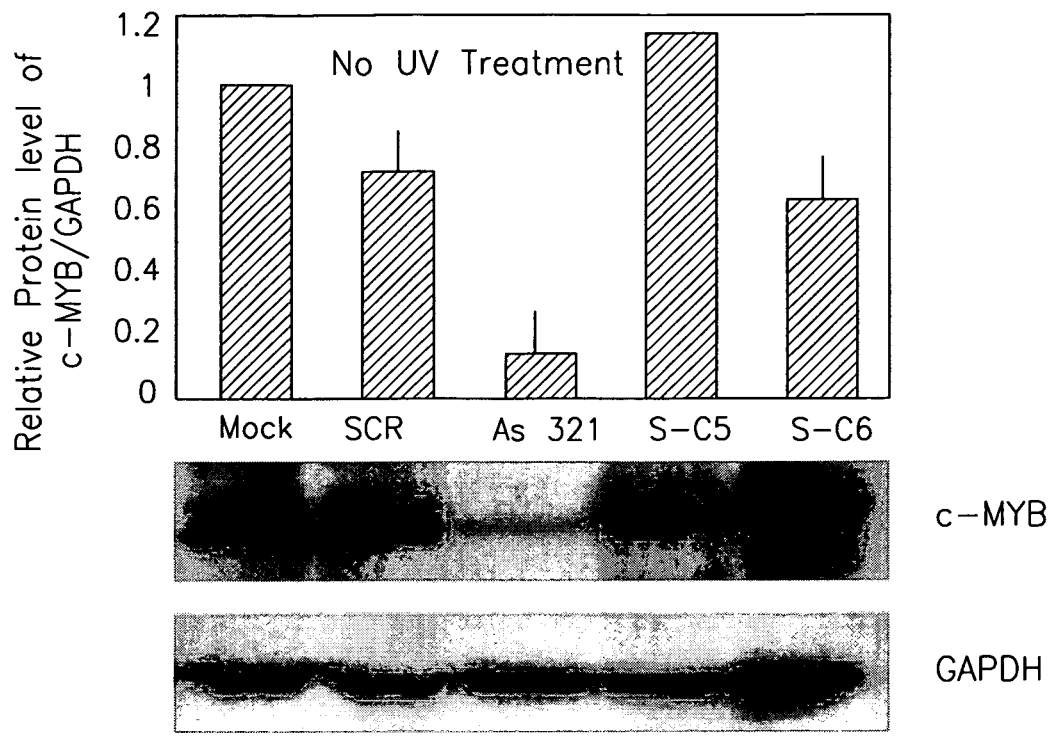
FIG. 26 shows c-MYB protein analysis by western blot performed on nucleofected K562 cells, either in the dark or treated with UV light for 5 min. Graph shows relative protein levels of c-MYB to GAPDH as quantified from western blots using ImageQuant. Mock cells were nucleofected with buffer in the absence of DNA, and other data were normalized to the Mock data, for which the ratio of gel intensities (c-MYB/GAPDH) was set to 1. Protein analysis was done 24 h post-nucleofection, with data from two independent trials. Error bars show deviation from the average.
Figure 26:
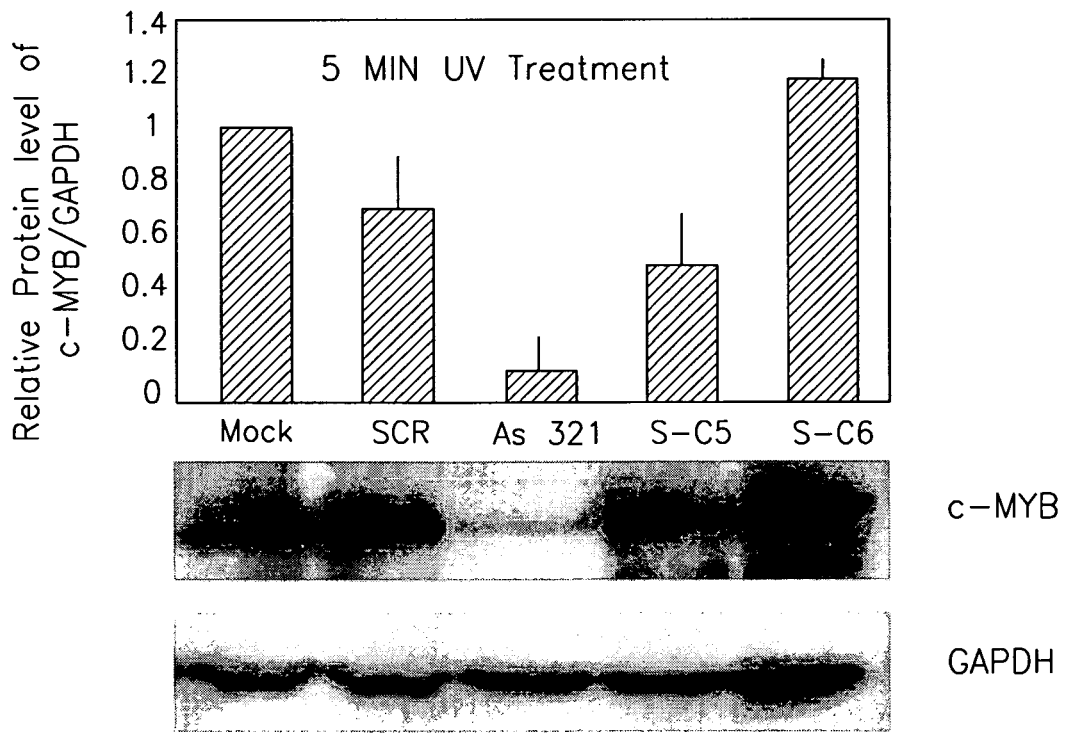

FIG. 26 shows data on cellular c-MYB protein levels. Western blots provided more variable data than RT-PCR, but confirmed many of the trends seen for mRNA levels. As was done similarly for FIG. 6, all c-MYB levels were corrected for variations in cell number and viability by taking a ratio of the c-MYB and GAPDH intensities. A decrease in c-MYB relative to GAPDH indicated gene-specific targeting effects. Most c-MYB protein knockdown was observed for AS 321, but S-C5 also showed substantial ability to photoregulate c-MYB levels within nucleofected K562 cells. c-MYB protein was reduced by 52% (compare lanes for S-C5, pre- and post-UV treatment). In contrast, Western blots for cells nucleofected with S-C6 indicated no obvious c-MYB protein knockdown when UV light was applied. This somewhat surprising result is discussed in greater detail below.

The thermal stability studies improved the understanding of RNA/DNA duplex formation and RNA hydrolysis in biochemical assays and could also be applied to understanding RNA cleavage within the cell. Less stable asODN/sODN duplexes (i.e., uncaged S-C5), which produced higher background levels of RNase H activity in biochemical assays, would reasonably perform better in complex biological systems. Although it is difficult to quantify precisely the concentration of accessible c-myb mRNA within the cell, the effective mRNA concentration was likely to be much lower for most constructs and target sequences. It was hypothesize that having a shorter 12-mer sODN (as in S-C5) was advantageous within the cell, where the asODN in a less stable asODN/sODN duplex would compete more effectively for a highly structured and relatively inaccessible mRNA target. Supporting this hypothesis were results with caged ncPNAs in zebrafish embryos shown in previous Examples, which indicated first that a very short (8-mer) sODN strand was very effective at blocking antisense activity. Importantly, the low melting temperature of the 8-mer sODN/ncPNA photo-generated duplex favored binding of the antisense ncPNA to the target mRNA and showed enhanced biological activity, relative to a more stable 12-mer sODN/ncPNA duplex.

In K562 cells, fine-tuning the thermal stability of the conjugate and photo-generated asODN/sODN duplex will also be required to achieve maximal photomodulation efficiency. From the data reported herein, it is apparent that the conjugates S-C5 and S-C6 were sufficiently stable to minimize background RNase H activity. Thus, ongoing efforts will focus on engineering photoproducts with less thermally stable asODN/sODN duplexes, in order to maximize the activity of the asODN. In this way, it should be possible to reduce c-MYB protein and c-myb mRNA to levels similar to those achieved with AS 321.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A photoactive oligonucleotide conjugate having the structure:

X-Y-Z wherein the X component is an antisense oligonucleotide of between 15 and 50 nucleotides in length; the Z component is a sense oligonucleotide that includes a sequence complementary to a first portion of at least 10 consecutive nucleotides of said antisense oligonucleotide; and the Y component is a photocleavable linker covalently attached therebetween, wherein the antisense oligonucleotide has a second portion of at least 5 consecutive nucleotides that is not complementary to the sense oligonucleotide and/or the antisense oligonucleotide is at least 5 nucleotides longer than the sense oligonucleotide, and wherein cleavage of said photocleavable linker results in a lower melting temperature ($T_m$) of the antisense oligonucleotide to the sense oligonucleotide of between about 20 to 50° C. of the cleaved conjugate relative to the uncleaved conjugate.

2. The conjugate of claim 1, wherein the antisense oligonucleotide is between 15 and 20 nucleotides in length.

3. The conjugate of claim 1, wherein the 5' end of the antisense oligonucleotide and the 3' end of the sense oligonucleotide each contain a region that is not complementary to the opposite strand.

4. The conjugate of claim 3, wherein the region is no less than 5 nucleotides in length.

5. The conjugate of claim 3, wherein the antisense oligonucleotide is a DNA, a peptide nucleic acid (PNA), a negatively charged peptide nucleic acid (ncPNA), a phosphorothioate DNA (PS-DNA), a phosphorodiamidate morpholino oligonucleotide (PMO), or a locked nucleic acid (LNA).

6. The conjugate of claim 1, wherein the photocleavable linker is capable of reacting with thiol and amine functionalities.

7. The conjugate of claim 1, wherein the photocleavable linker is 1-(5-(N-maleimidomethyl)-2-nitrophenyl)ethanol N-hydroxysuccinimide ester.

8. The conjugate of claim 1, wherein the photocleavable linker comprises a maleimido moiety.

9. The conjugate of claim 1, wherein the photocleavable linker comprises a N-hydroxysuccinimide ester moiety.

10. The conjugate of claim 1, wherein the sense oligonucleotide comprises a DNA, a peptide nucleic acid (PNA), a negatively charged peptide nucleic acid (ncPNA), a phosphorothioate DNA (PS-DNA), a phosphorodiamidate morpholino oligonucleotide (PMO), a locked nucleic acid (LNA), or 2'-O-methyl RNA (2'-OMe RNA).

11. A composition for reducing expression of a gene of interest in a subject comprising a photocleavable conjugate, wherein the conjugate comprises an antisense oligodeoxynucleotide (asODN) of between 15 and 50 nucleotides in length with at least 15 consecutive nucleotides which are no less than 85% complementary to the gene of interest, a sense strand complementary to a portion of at least 10 consecutive nucleotides of said asODN, and a photocleavable linker attached therebetween; wherein cleaving the photocleavable linker of the conjugate activates the asODN to react with the gene of interest, wherein cleavage of said photocleavable linker results in a lower melting temperature ($T_m$) of the antisense oligonucleotide to the sense oligonucleotide of between about 20 to 50° C. of the cleaved conjugate relative to the uncleaved conjugate, and wherein hybridization of the cleaved antisense oligonucleotide with the gene of interest is more energetically preferable than reassociation with the sense strand.

12. The composition of claim 11 wherein the sense oligonucleotide comprises a DNA, a peptide nucleic acid (PNA), a negatively charged peptide nucleic acid (ncPNA), a phosphorothioate DNA (PS-DNA), a phosphorodiamidate morpholino oligonucleotide (PMO), or a locked nucleic acid (LNA), or 2'-O-methyl RNA (2'-OMe RNA).

* * * * *